(12) United States Patent
Piestrup et al.

(10) Patent No.: US 11,090,509 B1
(45) Date of Patent: Aug. 17, 2021

(54) NEUTRON SOURCE WITH BEAM SHAPING APPARATUS FOR CANCER TREATMENT

(71) Applicant: Adelphi Technology, Inc., Redwood City, CA (US)

(72) Inventors: Melvin Arthur Piestrup, Redwood City, CA (US); Craig Mathew Brown, Santa Clara, CA (US); Jay Theodore Cremer, Jr., Palo Alto, CA (US); Charles Kevin Gary, Palo Alto, CA (US); David Lowndes Williams, Los Altos, CA (US); Allan Xi Chen, Daly City, CA (US); Glenn Emerson Jones, Jr., Pittsburg, CA (US); Yao Zong Guan, San Francisco, CA (US); Randall Scott Urdahl, Mountain View, CA (US); Adam Nathaniel Amoroso, Mountain View, CA (US)

(73) Assignee: Adelphi Technology, Inc., Redwood City, CA (US)

( * ) Notice: Subject to any disclaimer, the term of this patent is extended or adjusted under 35 U.S.C. 154(b) by 0 days.

(21) Appl. No.: 17/198,922

(22) Filed: Mar. 11, 2021

Related U.S. Application Data

(63) Continuation-in-part of application No. 17/032,211, filed on Sep. 25, 2020, now Pat. No. 10,955,365.

(51) Int. Cl.
*G01N 23/05* (2006.01)
*A61N 5/10* (2006.01)

(52) U.S. Cl.
CPC ......... *A61N 5/1048* (2013.01); *A61N 5/1001* (2013.01); *A61N 2005/109* (2013.01)

(58) Field of Classification Search
CPC ............... A61N 5/1048; A61N 5/1001; A61N 2005/109; A61N 5/1077; A61N 5/1081; C04B 41/4842; C04B 35/6455; C04B 41/84; C04B 41/83
See application file for complete search history.

(56) References Cited

U.S. PATENT DOCUMENTS

2019/0054319 A1* 2/2019 Wang .................. A61K 41/0095
2019/0351257 A1* 11/2019 Chen ........................ G21K 1/10

* cited by examiner

*Primary Examiner* — David P Porta
*Assistant Examiner* — Mamadou Faye
(74) *Attorney, Agent, or Firm* — Donald R. Boys; Central Coast Patent Agency LLC

(57) ABSTRACT

A cancer treatment apparatus has a neutron source generating neutrons exiting through a surface of a moderator block and an elongated beam-shaping apparatus (BSA) having a length and a circular cross section of a diameter less than the length, the BSA joined at one end to and projecting orthogonally from the surface of the moderator block of the neutron source, the BSA having a conically shaped element at an end away from the moderator block, the conically shaped element declining in diameter in a direction away from the moderator block. Neutrons produced by the neutron source enter the BSA at the surface of the moderator block, travel the length of the BSA, and exit the BSA through an aperture at the end of the BSA away from the moderator block.

18 Claims, 17 Drawing Sheets

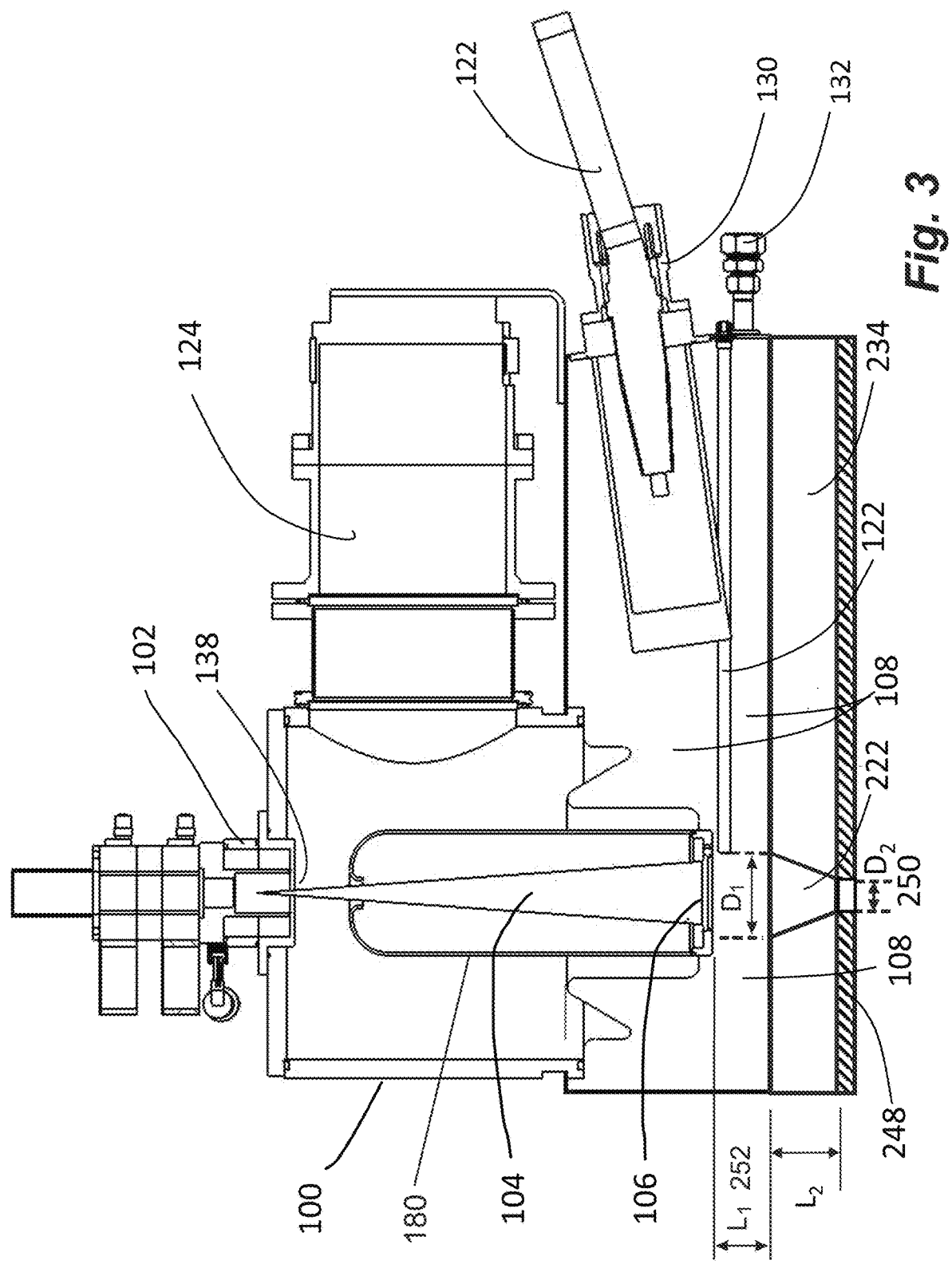

NEUTRON SOURCE WITH BEAM SHAPING APPARATUS FOR CANCER TREATMENT

CROSS-REFERENCE TO RELATED APPLICATIONS

The present application is a Continuation-in-Part of co-pending application of Ser. No. 17/032,211, filed Sep. 25, 2020. The disclosures of the parent case is incorporated herein at least by reference.

BACKGROUND OF THE INVENTION

1. Field of the Invention

This invention is in the technical area of apparatus and methods for Boron Neutron Cancer Therapy (BNCT) and pertains more particularly to improved beam shaping for neutron generators and application to subjects for treatment.

2. Description of Related Art

Boron Neutron Capture Therapy (BNCT) is not new in the art, as thermal neutrons have been used for cancer therapy for the destruction of cancer tumors. These neutrons interact with boron-10 that has been placed at the cancer site. The neutrons interact with the boron to produce fission events whereby alpha particles and lithium nuclei are created. These massive, ionized particles are then released, destroying the chemical bonds of nearby cancer tumor cells. At present the neutrons created in a reactor or accelerator pass through a moderator, which shapes the neutron energy spectrum suitable for BNCT treatment. While passing through the moderator and then the tissue of the patient, the neutrons are slowed by collisions and become low energy thermal neutrons. The thermal neutrons undergo reactions with the boron-10 nuclei at a cancer site, forming compound nuclei (excited boron-11), which then promptly disintegrate to lithium-7 and an alpha particle. Both the alpha particle and the lithium ion produce closely spaced ionizations in the immediate vicinity of the reaction, with a range of approximately 5-9 micrometers, or roughly the thickness of one cell diameter. The release of this energy destroys surrounding cancer cells. This technique is advantageous since the radiation damage occurs over a short range and thus normal tissues can be spared.

Gadolinium can also be considered as a capture agent in neutron capture therapy (NCT) because of its very high neutron capture cross section. A number of gadolinium compounds have been used routinely as contrast agents for imaging brain tumors. The tumors have absorbed a large fraction of the gadolinium, making gadolinium an excellent capture agent for NCT. Therefore, GNTC may also be considered as a variation in embodiments of the present invention.

The following definitions of neutron energy ranges, E, are used frequently by those skilled in the art of producing and using neutrons for medical, commercial and scientific applications: Fast (E>1 MeV), Epithermal (0.5 eV<E<1 Mev) and Thermal (E<0.5 eV) neutrons.

BNCT has the potential to treat previously untreatable cancers such as glioblastoma multiforme (GBM). In the US brain tumors are the second most frequent cause of cancer-related deaths for males under 29 and females under 20. GBM is nearly always fatal and has, until now, no known effective treatment. There are approximately 13,000 deaths per year due to primary brain tumors.

If conventional medicine is used where the glioblast is excised, new tumors almost invariably recur, frequently far from the original tumor site. Effective radiation therapy, therefore, must encompass a large volume and the radiation must be uniformly distributed. Conventional radiation treatment is usually too toxic to be of use against GBM.

For distributed tumors, effective radiation therapy must encompass a larger volume and the radiation must be uniformly distributed. This is also true of liver cancers. The liver is the most common target of metastases from many primary tumors. Primary and metastatic liver cancers are usually fatal, especially after resection of multiple individual tumors. The response rate for nonresectable hepatocellular carcinoma to traditional radiation treatment or chemotherapy is also very poor. However, recent results indicate that the thermal neutron irradiation of the whole liver with a $^{10}$B compound, to be bombarded with low-energy neutrons, could be a way to destroy all the liver metastases.

Recent research in BNCT has shown that neutron capture therapy can be used to treat a large number of different cancers. BNCT has been found to be effective and safe in the treatment of inoperable, locally advanced head and neck carcinomas that recur at sites that were previously irradiated with traditional gamma radiation. Thus, BNCT could be considered for a wider range of cancers. BNCT holds such promise because the dose to the cancer site can be greatly enhanced over that produced by γ-radiation sources. This is a consequence of the fact that the neutron-boron reaction produces the emission of short-range (5-9 um distance) radiation, and consequently normal tissues can be spared. In addition, boron can achieve a high tumor-to-brain concentration ratio, as much as ten or more, thereby preferentially destroying abnormal tissue.

BNCT has been tested using either nuclear reactors or accelerators to produce the neutrons, which are not practical or affordable for most clinical settings. Reactors also do not produce an ideal neutron spectrum and are contaminated with γ-radiation.

Low Voltage, Fusion neutron generators (LVFGs) permit a long-lived, easily moderated neutron source to be available for cancer treatment. However, compact neutron generators using the DD fusion reaction have emission that is isotropic and not directional, and, hence, focusing or collimating neutrons that are produced is not easily achieved. Further, most moderation materials and processes result in undesirable components such as gamma and higher energy neutrons. Moderating the fast neutrons to thermal energies also results in reduction of desired thermal neutron flux and brightness. Obtaining directional, high density flux of thermal neutrons on a target site has been difficult without the extensive losses of neutrons and an enlarged thermal neutron source.

Unlike reactors, the LVFG has qualities that can compensate for this issue, such as small source size, high neutron brightness, and low fast neutron energy (2.5 MeV). Small source size allows for easier collection and moderation of fast neutrons into either thermal or epithermal neutrons, thereby increasing neutron flux.

What is clearly needed in the art is a modular, relatively small LVFG that may be joined to unique collimating apparatus to produce a substantially focused beam of thermal neutrons, integrated with apparatus for engaging tumor sites on a subject body to effectively improve neutron delivery to a tumor site.

BRIEF SUMMARY OF THE INVENTION

In an embodiment of the invention a cancer treatment apparatus is provided, comprising a neutron source generating neutrons exiting through a surface of a moderator block, and an elongated beam-shaping apparatus (BSA) having a length and a circular cross section of a diameter less than the length, the BSA joined at one end to and projecting orthogonally from the surface of the moderator block of the neutron source, the BSA having a conically shaped element at an end away from the moderator block, the conically shaped element declining in diameter in a direction away from the moderator block. Neutrons produced by the neutron source enter the BSA at the surface of the moderator block, travel the length of the BSA, and exit the BSA through an aperture at the end of the BSA away from the moderator block.

In one embodiment the BSA further comprises an outer sleeve encasing a concentric inner sleeve encasing a bismuth disk in line with a sapphire crystal cylinder, and a funnel cavity within the conically-shaped element at the end away from the moderator block, such that neutrons exiting the moderator block through the surface proximate the BSA pass through the bismuth disk and the sapphire crystal, enter the funnel and are collimated through the funnel to exit through the aperture at the end of the BSA, providing a neutron beam with a spot size useful for neutron irradiation of a tumor.

In one embodiment the moderator block is made of one or a combination of high-density polyethylene (HDPE), Teflon, Ultra High Molecular Weight polyethylene, or graphite. Also, in one embodiment the outer sleeve is high-density polyethylene (HDPE) or Ultra High Molecular Weight polyethylene. And in one embodiment the length of the BSA is between three inches and ten inches, inclusive.

In one embodiment of the invention the outside diameter of the BSA is between three-quarters of an inch and two inches inclusive. Also, in one embodiment the length of the funnel is from 1 to 10 inches, inclusive. And in one embodiment the aperture at the end of the BSA away from the moderator block has a diameter of from 0.38 inches to 0.75 inches inclusive.

In another aspect of the invention a method for treating a subject for a tumor at the PONS is provided, comprising joining an elongated beam-shaping apparatus (BSA) having a length and a circular cross section of a diameter less than the length to project orthogonally from a first end from a surface of a moderator block of a neutron source generating neutrons exiting through the surface of a moderator block into the BSA, the BSA having a conically shaped funnel at an end away from the moderator block, the conically-shaped element declining in diameter in a direction away from the moderator block and ending at an emission aperture at a second end away from the moderator block, placing the subject on a support proximate to the neutron source, positioning the BSA in an oral cavity of the subject with the emission aperture proximate the tumor site at the PONS, and irradiating the tumor for a period of time with neutrons emitted from the emission aperture.

In one embodiment the method further comprises a step for ensuring the neutron source is powered off, not generating neutrons, during the time the subject and the apparatus are manipulated to position the BSA in the oral cavity, and a step for powering on the neutron source to treat the tumor after the subject and the apparatus positioned for treatment. Also, in one embodiment the method further comprises an outer sleeve encasing a concentric inner sleeve encasing a bismuth disk in line with a sapphire crystal cylinder, and a funnel cavity within the conically-shaped element at the end away from the moderator block, and wherein neutrons exiting the moderator block through the surface proximate the BSA pass through the bismuth disk and the sapphire crystal, enter the funnel and are collimated through the funnel to exit through the aperture at the end of the BSA. In one embodiment the moderator block is made of one or a combination of high-density polyethylene (HDPE), Teflon, Ultra High Molecular Weight polyethylene, or graphite. And in one embodiment the outer sleeve is high-density polyethylene (HDPE) or Ultra High Molecular Weight polyethylene.

In yet another aspect of the invention a method for treating a subject for-tumors at the prostate gland is provided, comprising joining an elongated beam-shaping apparatus (BSA) having a length and a circular cross section of a diameter less than the length to project orthogonally from a first end from a surface of a moderator block of a neutron source generating neutrons exiting through the surface of a moderator block into the BSA, the BSA having a conically shaped funnel at an end away from the moderator block, the conically-shaped element declining in diameter in a direction away from the moderator block and ending at an emission aperture at a second end away from the moderator block, placing the subject on a support proximate to the neutron source, positioning the BSA in an anal cavity of the subject with the emission aperture proximate the tumor site at the prostate gland, and irradiating the tumor for a period of time with neutrons emitted from the emission aperture.

In one embodiment this method further comprises a step for ensuring the neutron source is powered off, not generating neutrons, during the time the subject and the apparatus are manipulated to position the BSA in the oral cavity, and a step for powering on the neutron source to treat the tumor after the subject and the apparatus positioned for treatment. In one embodiment the method further comprises an outer sleeve encasing a concentric inner sleeve encasing a bismuth disk in line with a sapphire crystal cylinder, and a funnel cavity within the conically-shaped element at the end away from the moderator block, and wherein neutrons exiting the moderator block through the surface proximate the BSA pass through the bismuth disk and the sapphire crystal, enter the funnel and are collimated through the funnel to exit through the aperture at the end of the BSA. In one embodiment the moderator block is made of one or a combination of high-density polyethylene (HDPE), Teflon, Ultra High Molecular Weight polyethylene, or graphite. And in one embodiment the outer sleeve is high-density polyethylene (HDPE) or Ultra High Molecular Weight polyethylene.

BRIEF DESCRIPTION OF THE SEVERAL VIEWS OF THE DRAWINGS

FIG. 3 is a cross section view of the LVFG, its pre-moderator, and a convergent funnel for a small area source in an embodiment of the invention.

DETAILED DESCRIPTION OF THE INVENTION

Figure 1A:
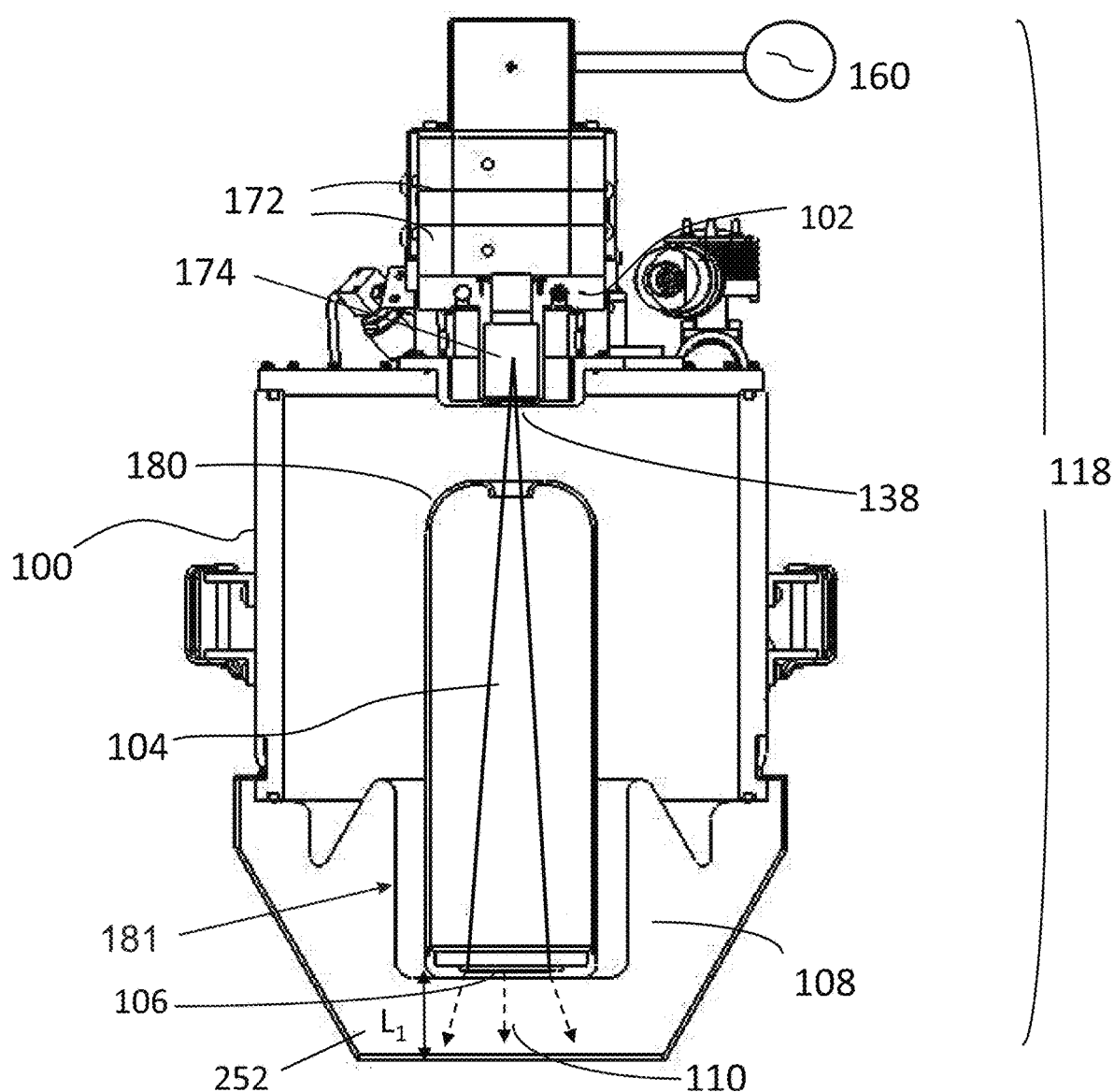
FIG. 1A is a transverse cross section of a modular neutron generator in an embodiment of the present invention.
Figure 1B:
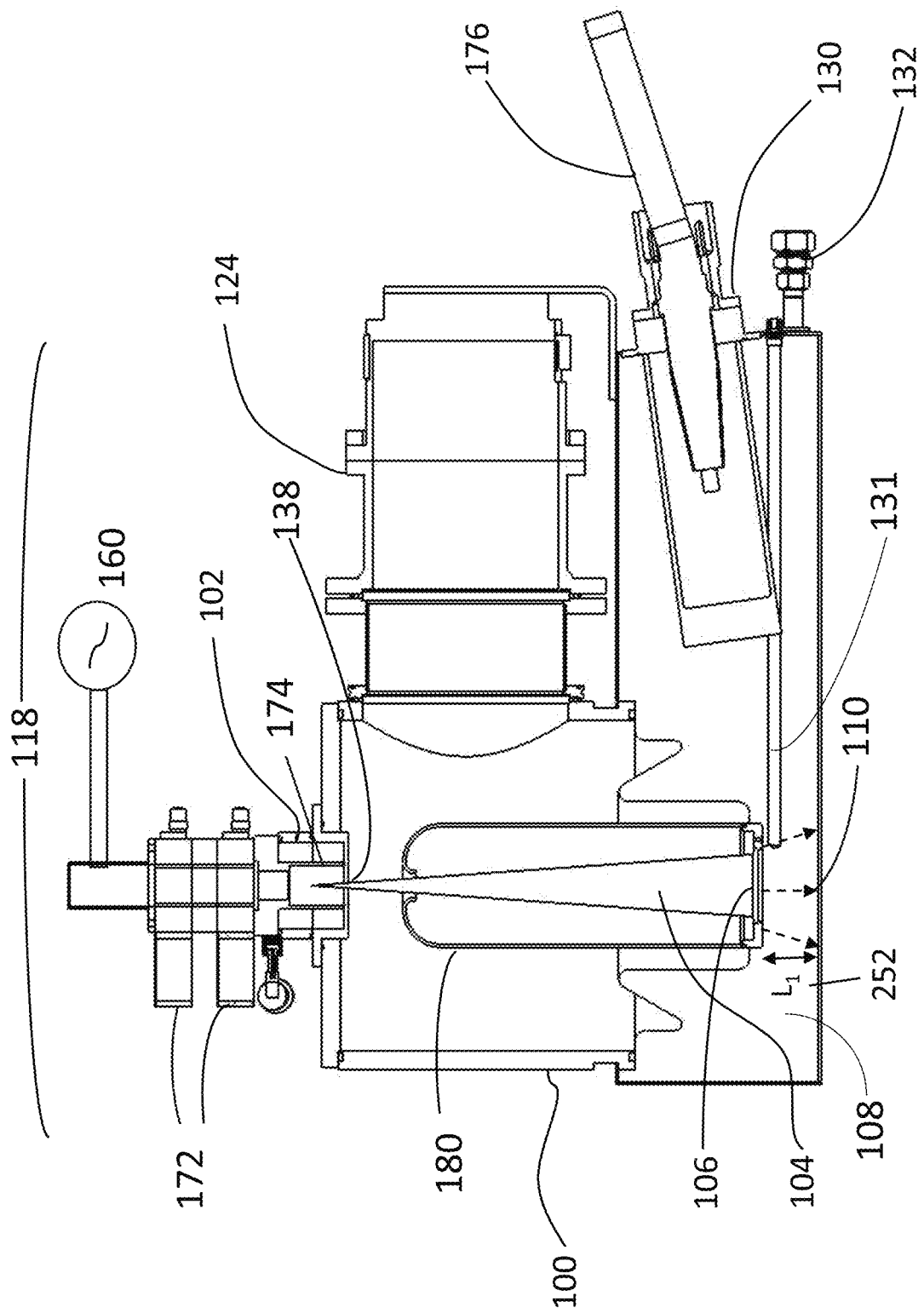
FIG. 1B is a longitudinal cross section of the modular generator of FIG. 1A.

FIGS. 1A and 1B are cross-sectional views of a modular neutron generator 118 known to the inventors designed to produce a substantial flux of thermal neutrons. Modular generator 118 comprises a pre-moderator 108 that is made of material known to moderate energy of fast neutrons to thermal energies. In most embodiments for thermal neutron production the pre-moderator may be a shaped, solid block of material such as High-Density Polyethylene (HDPE) or Ultra High Molecular Weight (UHMW) polyethylene. Selection of material and its thickness is determined at least in part by the desired neutron spectrum (e.g., thermal or epithermal) and desired neutron yield.

Modular generator 118 has four important elements in this example: (1) a deuterium ion source 102, (2) an acceleration chamber 100, through which deuterium ions 104 are accelerated, and (3) a titanium target 106 that is bombarded by the deuterium ions to produce high-energy neutrons 110. Deuterium ion source 102 has an attached microwave source 160 in the implementation, and microwave slug tuners 172. In operation Deuterium gas is leaked slowly into a plasma ion chamber 174 at an upper end of the acceleration chamber, where microwave energy ionizes the gas, creating deuterium $D^+$ ions 104. The gas is ionized by microwave energy, and Deuterium ions ($D^+$) 104 are created and accelerated through an ion extraction iris 138 into acceleration chamber 100, and through an electron suppression shroud 180 which deflects back-streaming electrons from being accelerated back into the plasma source, which could damage the apparatus. Electrons are created by collisions of the $D^+$ ions in the deuterium gas that are being created in the acceleration chamber.

The deuterium ions are positively charged, and target 106 is negatively charged to a level of from 120 kV to 220 kV, and the $D^+$ ions are strongly attracted to negatively biased titanium (Ti) target 106. Acceleration chamber 100 is connected to a turbo vacuum pump 124 that provides a modest vacuum in one embodiment of about $10^{-6}$ Torr, minimizing scattering of the $D^+$ ions as they travel from extraction iris 138 to target 106. Titanium target 106 is positioned in a cavity 181 at the bottom of the chamber, the cavity formed in the pre-moderator material. Pre-moderator 108 has a passage for a high voltage cable and fluid cooling channels to and from the target. Pre-moderator 108 acts as a high-voltage insulator and as a mechanical support for the target at a high negative bias. When in operation the $D^+$ ions in the ion beam are attracted to the titanium target 106, where fast neutrons are produced in a resulting DD fusion reaction.

A major issue for fusion sources using the Deuterium-Deuterium (D-D) reaction to produce fast neutrons that must be moderated to thermal neutron energies is that fast and epithermal neutrons as well as high energy gamma emission are usually part of the moderation of the fast neutrons to thermal energies. These components can accompany the thermal neutrons penetrating the absorbent material of the iris and may effectively increase the aperture size D if the extraneous radiation can penetrate the iris materials, blurring the desired image.

In large reactors, thermal neutrons have been obtained which have mixtures of thermal, epithermal, and fast neutrons along with gamma and x-rays. Applications such as neutron radiography and radiotherapy usually require the neutron energy to be confined to single neutron energy bands without x-ray or gamma components. There need be methods to eliminate the unwanted radiation components.

Modular DD fusion generator 118 in embodiments of the present invention uses a small titanium target (e.g., a 5-7 cm diameter disk of titanium backed by water-cooled copper fins) to produce neutrons. FIGS. 1A and 1B are cross-sectional drawings of a modular neutron generator to produce maximum thermal neutrons. The target is supported directly on the pre-moderator, which is an integral part of the apparatus in this implementation. The Ti target may be attached with fasteners to the pre-moderator block and may be sealed to the block with an O-ring. Targets in embodiments of the invention can be easily manually removed and replaced. They also have a long lifetime and have been tested for over 4000 hours with no failures.

In the following descriptions reference is made to accompanying drawings that form a part of the disclosure and teaching of the present invention, and which illustrate specific embodiments in which the invention may be practiced. It is to be understood that other embodiments may be utilized, and structural changes may be made without departing from the scope of the present invention.

The accelerator structure in embodiments of the invention is compact and includes a pre-moderator 108 that adds only about 4-5 cm of High-Density Polyethylene (HDPE) or 15-20 cm of polytetrafluoroethylene (PTFE) Teflon to produce a first stage of neutron beam tailoring in embodiments of the invention. The pre-moderator in these embodiments is an integral part of each modular generator, as is taught below with reference to several figures. Other short-length attachments are added to the pre-moderator to further improve the neutron beam in beam purity, size and shape, making the modular neutron generator a highly versatile source of neutrons. A primary application for the unique apparatus taught in this application is thermal neutron radiography, which requires a small source size, high neutron yield (n/cm²) and high beam purity. High thermal neutron beam purity is achieved in embodiments of the invention by minimizing other neutron and photon components that may be introduced during the DD fusion process and moderation of the 2.5 MeV neutrons to thermal energies. The filtering process is accomplished using neutron filters; both "low pass" and "high pass" filters. To maximize the resulting neutron flux and minimize the neutron source size, these filters and collimators are minimalized in length and proximity to the neutron generator. This results in a highly compact and useful neutron source for many applications.

As is known for most radiation sources, a small source size is required for image clarity and sharpness. "Geometric un-sharpness" or "blur" refers to loss of image detail caused by the finite size of the source diameter. This is true of sources of radiation such as x-ray tubes, where an electron beam of diameter D strikes the anode (e.g., tungsten target) of the x-ray tube, producing a source size of diameter D. In other sources of radiation used for radiographic imaging (example synchrotron radiators or plasma pinch sources of x-rays), the spot or source size D can be defined by the either a slit or metal aperture that defines where the x rays or neutrons are being emitted. In the present invention, the aperture is defined by an exit aperture D2 of a funnel or conical aperture.

The source or spot size can result in "geometric un-sharpness", "blur", or the loss of image detail caused by the finite size of the neutron emission size of diameter $D_2$. In neutron sources the spot size $D_2$ is defined by an exit aperture after the neutrons have been moderated to thermal neutron energies. The convergent aperture is defined by an exit aperture which can be made of different materials, such as HDPE and graphite, which result in collection and collimation of the thermal neutrons.

Figure 2:
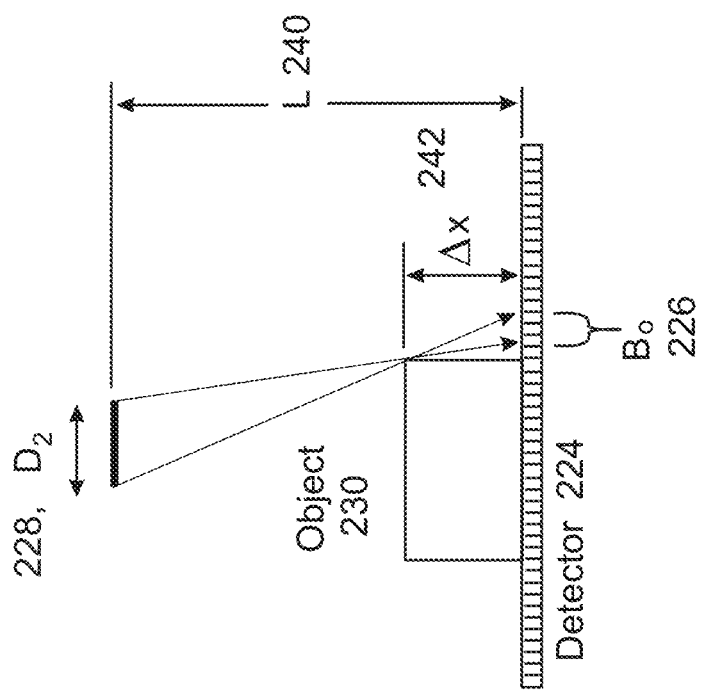
FIG. 2 is a diagram showing "geometrical un-sharpness" or blur in radiography using neutron sources.

As shown in FIG. 2 with simple geometry, minimum blur ($B_o$, 226) may be achieved if the neutron source-to-detector distance L, 240, and the source-emission diameter, $D_2$, 228, results in a small $D_2$/L. This permits a resolution of $\Delta x(D_2/L)$ for an object that is $\Delta x$ thick 242. For higher resolution (less blur $B_o$, 226) this relationship requires the source diameter $D_2$ to be small as possible and as far from the detector distance, L 240, as possible. Placing an aperture over the neutron source that limits source size $D_2$ will reduce the flux density (N/sec-cm²) where N is the number of neutrons per see that pass through the aperture to the detector. The optimum is to reduce $D_2$ without loss of neutrons. Focusing optics achieve this for photons, but for neutrons in the thermal energy range, this is difficult in a short distance L, without loss of neutrons from an ever-expanding neutron beam.

Thermal neutron collection can be achieved with a funnel 222 (FIG. 3) to both collect and channel neutrons into a small spot size $D_2$ with increased thermal flux at the exit $D_2$ of the funnel. The compact DD fusion source with a short (4-5 cm) moderator slows the fast 2.5 MeV neutrons to thermal energies in a short distance from the fast neutron source (the titanium target). The neutrons are then collected by a relatively short (e.g., $L_2$=3 to 4 cm) funnel shape formed into a slab of HDPE. Both moderation and scattering continue to occur along the funnel length L. Simulations show that this results in an increase in flux 2 to 3 times and spot sizes of 1 to 3 cm in diameter depending on the geometry of the cone and size of the fast neutron emitter (Ti target).

Compactness of the DD fusion generator, and shortness of the pre-moderator to produce and collect thermal neutrons also allow for the use of other devices in the neutron beam. These devices include short lengths of sapphire crystals and bismuth which can reduce fast neutrons and gamma emission in the neutron beam, thus cleaning up the beam and achieving a relatively pure beam of thermal neutrons.

In fusion devices, such as the LVFG in the present invention, the number of neutrons is limited. The use of a compact fusion generator with relatively small spot sources of neutrons permits neutron filters to also be compact and close together. The modular generator combines multiple functions that were separate functions in the prior art. These integrated functions include both neutron production and neutron energy band selection. This method shortens the overall length of the device and ensures high fluxes.

As was shown in FIG. 2, a critical requirement for image resolution is a small diameter source size of high neutron yield. FIG. 3 is a cross section of the neutron generator. In one embodiment a simple Beam Shaping Apparatus (BSA) in the form of funnel 222 is added, which may produce a small source size for radiography. In one embodiment the convergent funnel has a base diameter $D_1$ of 6 cm and exit opening $D_2$ of 1.5 cm. The funnel collects thermal neutrons being emitted by pre-moderator 108. The section of FIG. 3 is taken along an axis of an acceleration chamber 100 for ion beam generation and at a right angle to the axis of a turbo vacuum pump, 124, that is part of the modular generator.

In one embodiment an input aperture $D_1$ (252) of the funnel 222 is placed approximately at the $L_1$=5.5 cm away from the titanium target 106 whose diameter is 6 cm. This location is where the thermal neutron flux has been shown to be maximum and where collecting the thermal neutrons maximizes the neutrons at the exit aperture $D_2$, at least for this particular example.

As shown in FIG. 3, a short Beam Shaping Assembly (BSA) in the shape of funnel 222 is provided after Ti target 106 and the short moderator or pre-moderator 108, where the thermal neutrons may be collected by a large aperture $D_1$ and directed to a smaller aperture $D_2$ at the end of funnel 222. In a simple embodiment, funnel 222 is an inverted cone machined into the BSA support structure (or plate) 234 made of HDPE as shown in perspective view FIG. 3 with an entrance aperture $D_1$ and an exit aperture $D_2$. Cone-shaped funnel 222 in this embodiment is formed into the plate 234 of HDPE. Other materials such as Teflon, UHMW polyethylene, or graphite can be used for the plate. As shown in FIG. 3, an exit aperture 250 is also machined in the shielding 248 to define the thermal neutrons coming from the exit aperture.

After collection at aperture $D_1$, the resulting thermal neutron beam exits at aperture $D_2$, providing an increased flux and smaller source size for the thermal neutrons when compared to a simple pre-moderator.

Figure 4A:
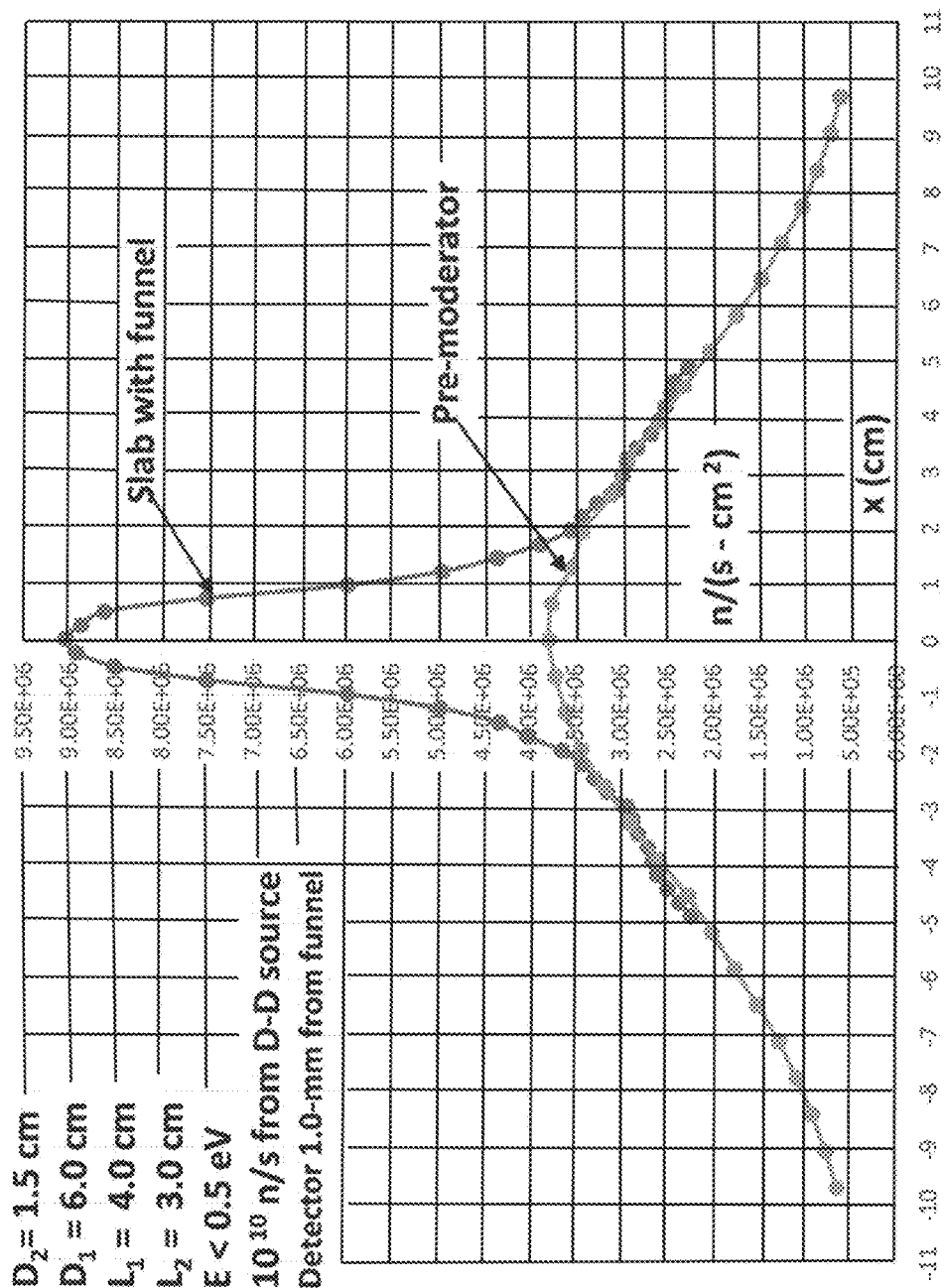
FIG. 4A illustrates thermal neutron yield (n/sec-cm$^2$) as a function of distance x across an axis of the convergent funnel of a simple beam-shaping assembly (BSA) in an embodiment of the invention.

FIG. 4A is a plot of flux density vs. lateral dimension in cm. at $D_2$ in one example. In the example of FIG. 4A, the spot size is roughly 1.5 cm at diameter ($D_1$). Without the funnel 222 the diameter of the source size would be a disc 6 cm in diameter and expanding (FIG. 4). The use of the moderator in direct or near contact with Titanium target 106 is to produce a maximum thermal neutron flux at the top aperture $D_1$ of the funnel 222. Adding a funnel 222 of modest length ($L_2$=4 cm in this example) directly on to the pre-moderator permits a maximum number of neutrons and higher thermal neutron flux to be collected and a smaller source size to be obtained. The close stacking of the pre-moderator 108 and the BSA (Funnel 222 in HDPE slab 234) permits a maximum number of thermal neutrons to be obtained with a small source size. FIG. 4A clearly illustrates the beneficial effect of the slab with the funnel.

To reduce the size of the thermal neutron beam emitted by the HDPE moderator at its maximum thermal neutron flux (n/sec-cm$^2$), funnel aperture 222 is added along the axis of the generator 118 as defined by direction of the D$^+$ ion beam 104, and the titanium target 106. As shown in FIGS. 3A and 3B, the dimensions of the apertures in this example are: $D_2$=1.5 cm, $D_1$=6.0 cm, $L_1$=4.0 cm, $L_2$=3.0 cm., E<0.5 eV. The plot in FIG. 4 is from a Monte Carlo Neutral Particle (MCNP) code simulation for these parameters. For the case with no funnel, the moderator shows a beam spot of FWHM of 10 cm in diameter. With the funnel 222 in place, the FWHM of the emission is roughly 2 cm in diameter, defined by a known technique called Full Width Half Maximum (FWHM) and the neutron flux is 2 times larger than an uncollimated neutron beam." The source size after the funnel has a full width half maximum of 2 cm, whereas for pre-moderator only, it is 10 cm. One can achieve a high resolution if the source is at an enough distance L, and small enough emission size diameter, $D_2$, to have a small $D_2$/L. This permits a resolution of $\Delta x(D_2/L)$ for an object that is $\Delta x$=1 mm thick. For a $D_2$ of 1.5 cm and an L=20 cm, the resolution is 0.1 mm.

Figure 4B:
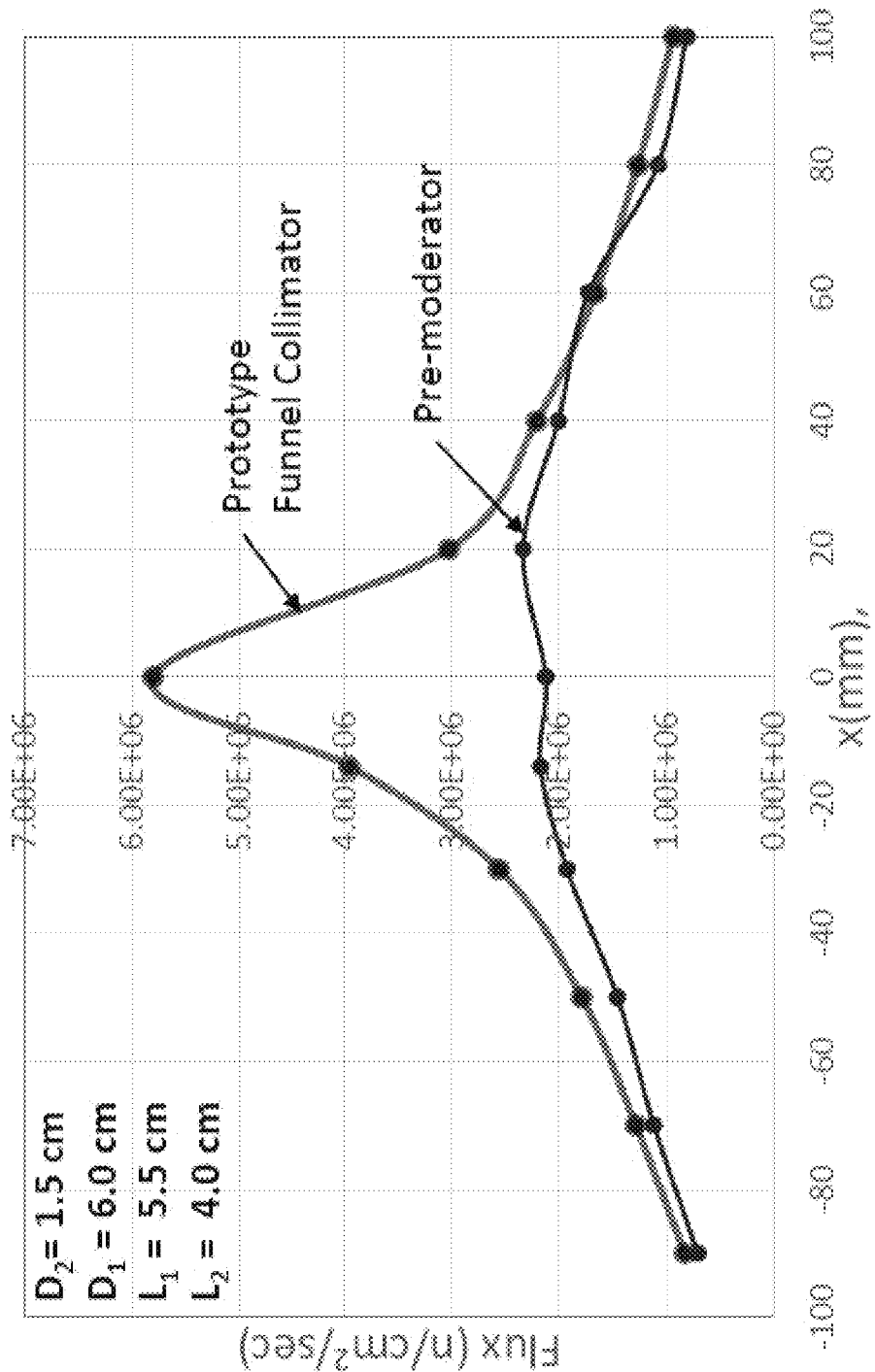
FIG. 4B illustrates measured thermal neutron yield (n/sec-cm$^2$) as a function of distance x across the axis of the convergent funnel of the simple BSA (Slab with funnel) and for the case of no funnel and the moderator with the thickness $L_1+L_2=9.5$ cm.

A prototype of the apparatus has been built and tested at the time of filing the present patent application. The apparatus is shown in FIGS. 3A and 3B with a funnel collimator as shown in the two figures, as described above. The dimension of the prototype funnel collimator are $D_1$=6 cm and $D_2$=1.5 cm with $L_1$=5.5 cm and $L_2$=4 cm. These dimensions may be different in other embodiments. The method of detection of the thermal neutron is a linear array of small chips of NaCl. These chips were activated by the in-coming thermal neutrons for a measured length of time. The radioactive flux was then determined by neutron spectrographic means. The results are shown in FIG. 4B. The general shape and magnitudes are comparable with the simulated results of FIG. 4A. The peak flux of FIG. 4B is smaller (6×10$^6$ n/sec-cm$^2$) than that of the simulation of FIG. 4A. (9×10$^6$ n/sec-cm$^2$). The differences are from the resolution of the detectors (measured vs simulated). The simulation of FIG. 4A used a shorter pre-moderator, $L_1$=4.0 cm. vs $L_1$=5.5 cm. However, in both case $L_2$=5.5 cm and the comparison between 4A and 4B shows that the HDPE funnel BSA is indeed effective as a method of collimation.

In examples of BSAs, convergent collimators are used. Other geometries can be used such as divergent collimators, which reverse the direction of the truncated cone. These have been used throughout the nuclear reactor source industry. Some collimators have a divergent-convergent shape, which can result in a shorter BSA length and higher thermal neutron flux.

Figure 5:
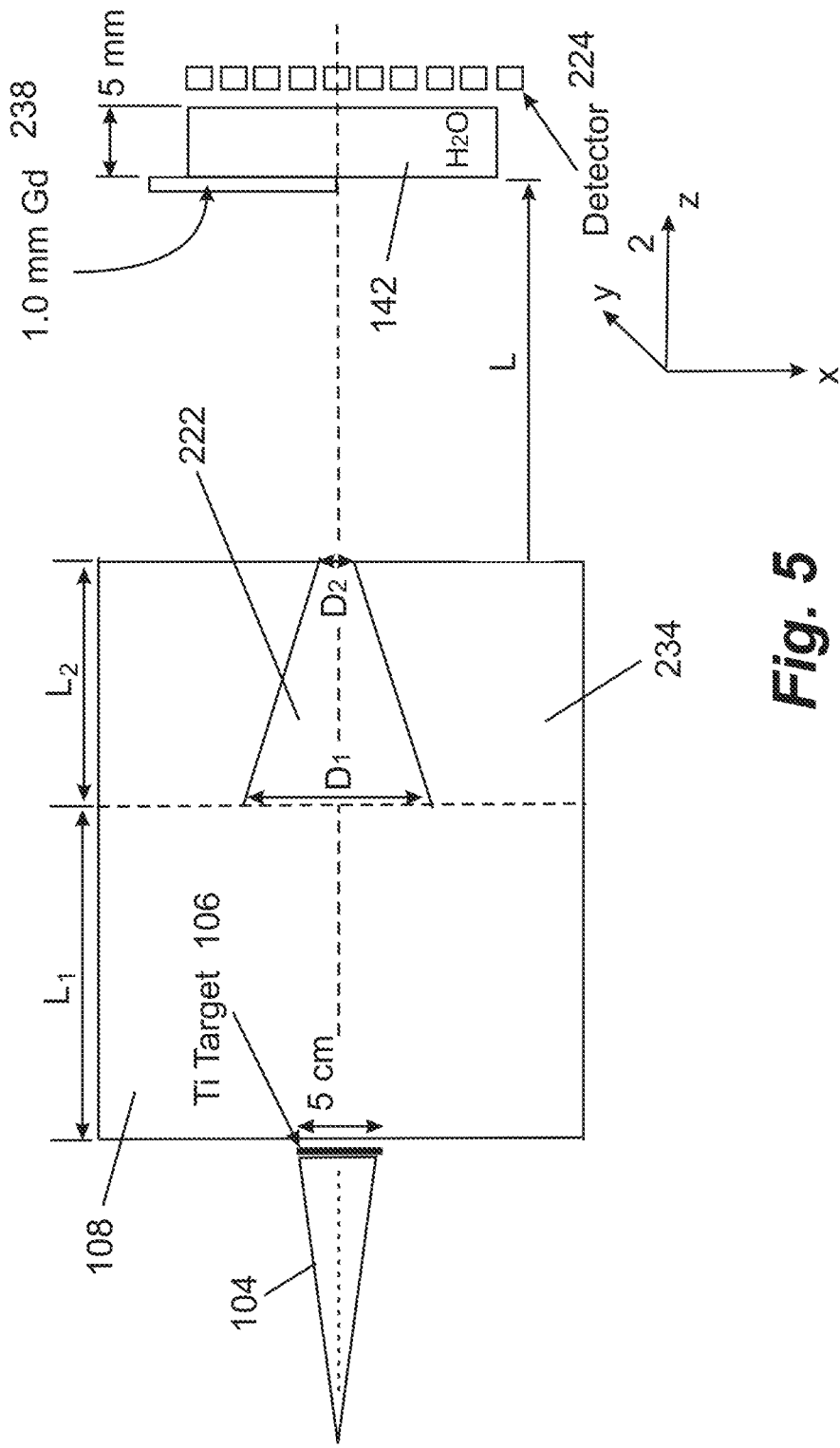
FIG. 5 is a cross sectional view of components required for producing a knife edge image for a computer simulation in an embodiment of the invention.

To see how well the conical aperture source performs, an image of a 1.0 mm thick Gadolinium (Gd) knife edge 238 is simulated, placed in front of a detector array 224 made of 5.0 mm of H$_2$O, 142, as shown in FIG. 5. For this calculation, the desirable image properties are (a) a flux of greater than 10$^3$ n/(s-cm$^2$), and (b) a desired resolution is 1 mm, with the contrast of an order of magnitude or greater.

To see how well the conical aperture neutron source works, an image of a 1.0-mm-thick-Gadolinium (Gd) knife edge 238 with a conical BSA 222 is simulated. Water (5-cm, 240), is used to simulate materials in the detector 246 which scatter the thermal neutrons. The Gd knife edge 238 is placed on the upstream side and in front of the H$_2$O, 240 to determine resolution and contrast. With the arrangement shown in FIG. 5, L is the distance between the BSA 222 and the Gd-knife edge 238. In all the simulations shown in this submission, a diode array detector 246 is assumed to be at a distance of 1.0 mm from the back of the H$_2$O 240. The BSA 222 is an air cone embedded (machined in HDPE with an entrance aperture of $D_1$=6 cm and an exit aperture of $D_2$=1.5 cm). The neutron flux (n/cm$^2$-sec) is found using a Monte Carlo Neutral Particle (MCNP) simulation shown in FIG. 6, which compares the thermal (E<0.5 eV) and fast (E>0.5 eV) energy neutron flux components.

Figure 6:
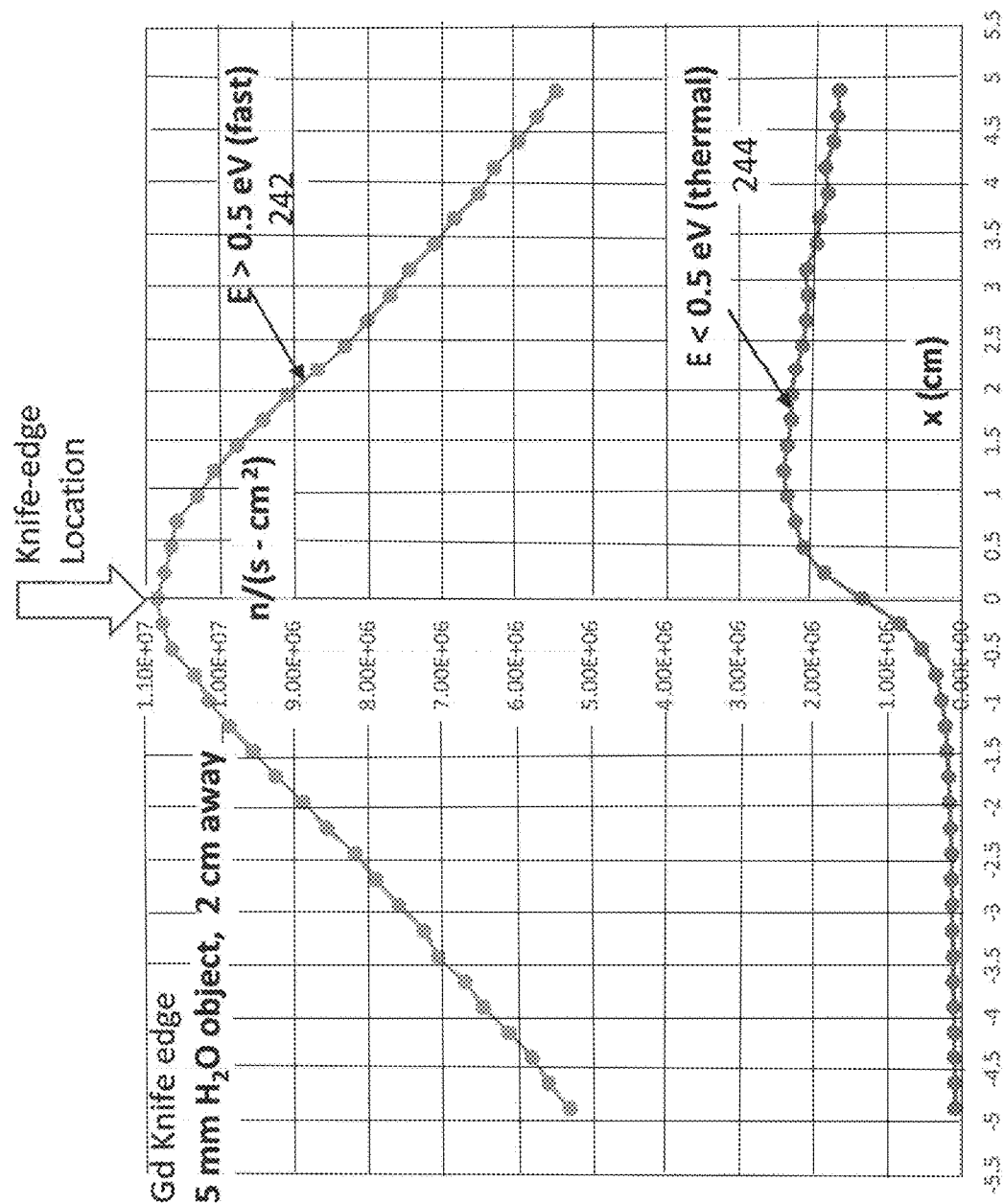
FIG. 6 illustrates a computer simulation of a knife edge made of Gadolinium (Gd) for fast neutrons (E>0.5 eV) and thermal neutrons (E<0.5 eV) in an embodiment of the invention.

To attempt to achieve these properties, various modulator and BSA arrangements are considered. The object is a 1.0-mm-thick Gd knife edge, 238, backed by 5-mm of H$_2$O, 240, and is placed on the upstream side of the H$_2$O to determine resolution and contrast. In the generator, the ion beam 104 strikes a 5-cm diameter Ti target 106 and 2.5-MeV neutrons are emitted into the pre-moderator of thickness $L_1$=4 cm. FIG. 6 shows the simulated Monto Carlo in Transport (MCNP) thermal flux 244 and fast 242 neutron fluxes as a function of x across the detector array 224. For this arrangement, the resolution is calculated to be 8.5 mm. Other simulations with somewhat different parameters gave resolutions of 3.3 mm.

The fast neutrons created from the moderation process are shown in the top curve in FIG. 6. Note, the fast neutrons 242 in the simulation are not being contrasted across the Gd knife edge. Indeed, most neutron detectors cannot easily distinguish between fast and thermal neutrons. However, separation between the fast and the thermal neutrons can be achieved by pulsing the neutron beam. The generator can be modulated by pulsing the ion beam, interrupting the microwave power that is creating the D$^+$ ions. Pulses as short as 10 μsecs have been produced by the inventors using this method. The fast neutrons are created at the titanium target and then pass through 4 cm of the HDPE pre-moderator where approximately 50% are reduced to thermal energies. For a 10 μsec pulse of neutrons, the difference in speed (2.2 km/sec for thermals and 1.4×10$^4$ km/sec for fast neutrons) results in thermal neutrons lagging by 20 μsec when they reach the detector at 20 cm from the aperture. Timing of the reading of the fast and thermal neutron pulses detected by a charge-coupled device (CCD) camera allows to distinguish between the two images; one caused by the thermal neutrons and the other by the fast neutrons. The neutron source properties are sufficient neutron flux (e.g., 10$^3$ n/(s-cm$^2$) or greater coming from a small spot size. Millimeter resolution is desired having an image contrast of an order of magnitude or greater.

With the arrangement in FIG. 5 and L=2.0 cm, FIG. 6 shows thermal and higher energy neutron flux. For these parameters, the flux is good, the contrast is good, the transverse dimension is good, but the resolution is 8.5 mm.

Figure 7A:
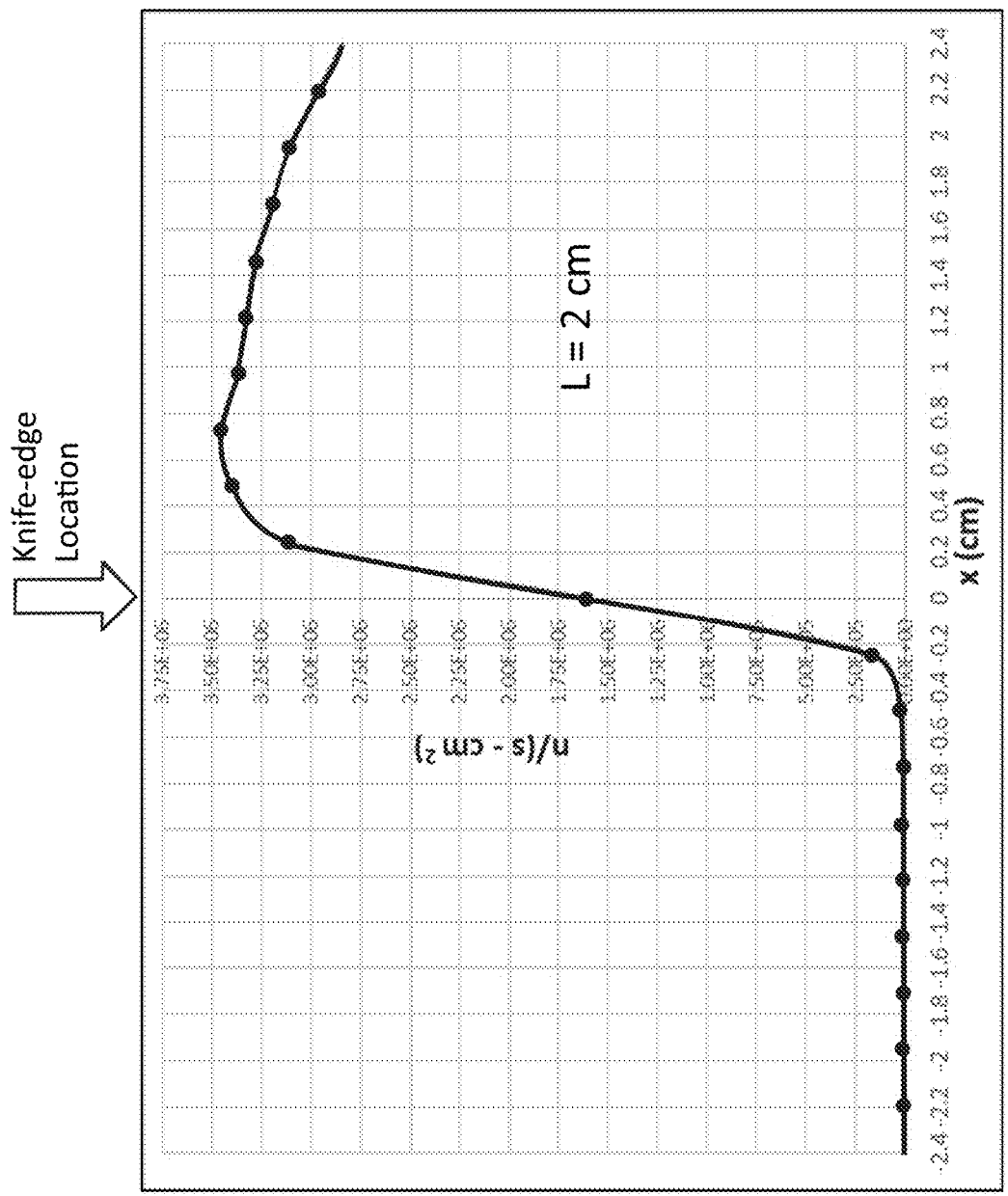
FIG. 7A shows image flux as a function of x, the transverse distance across a detector array in an embodiment of the invention.
Figure 7B:
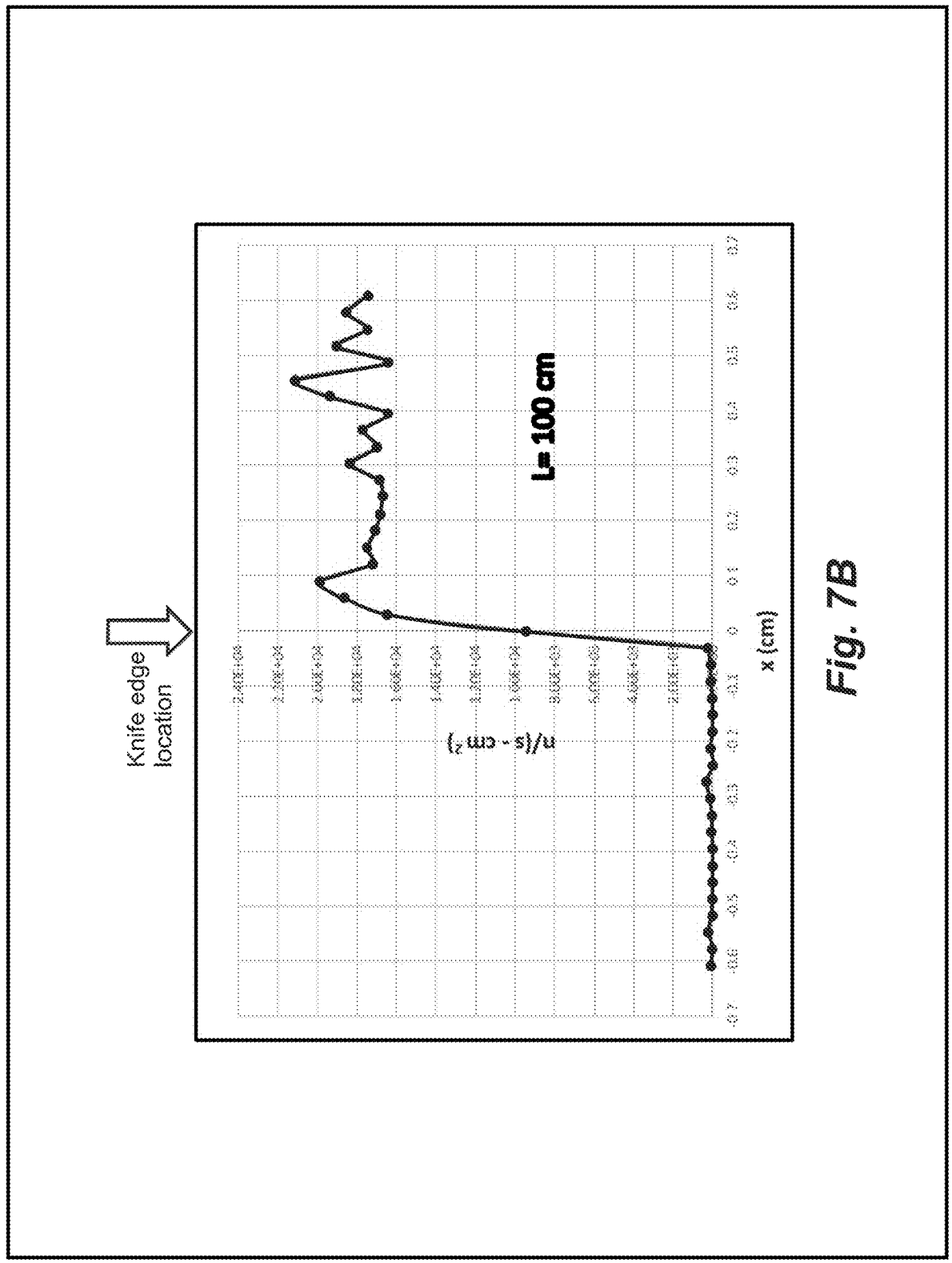
FIG. 7B shows image flux as a function of x, the transverse distance across the detector array in an embodiment of the invention.
Figure 8:
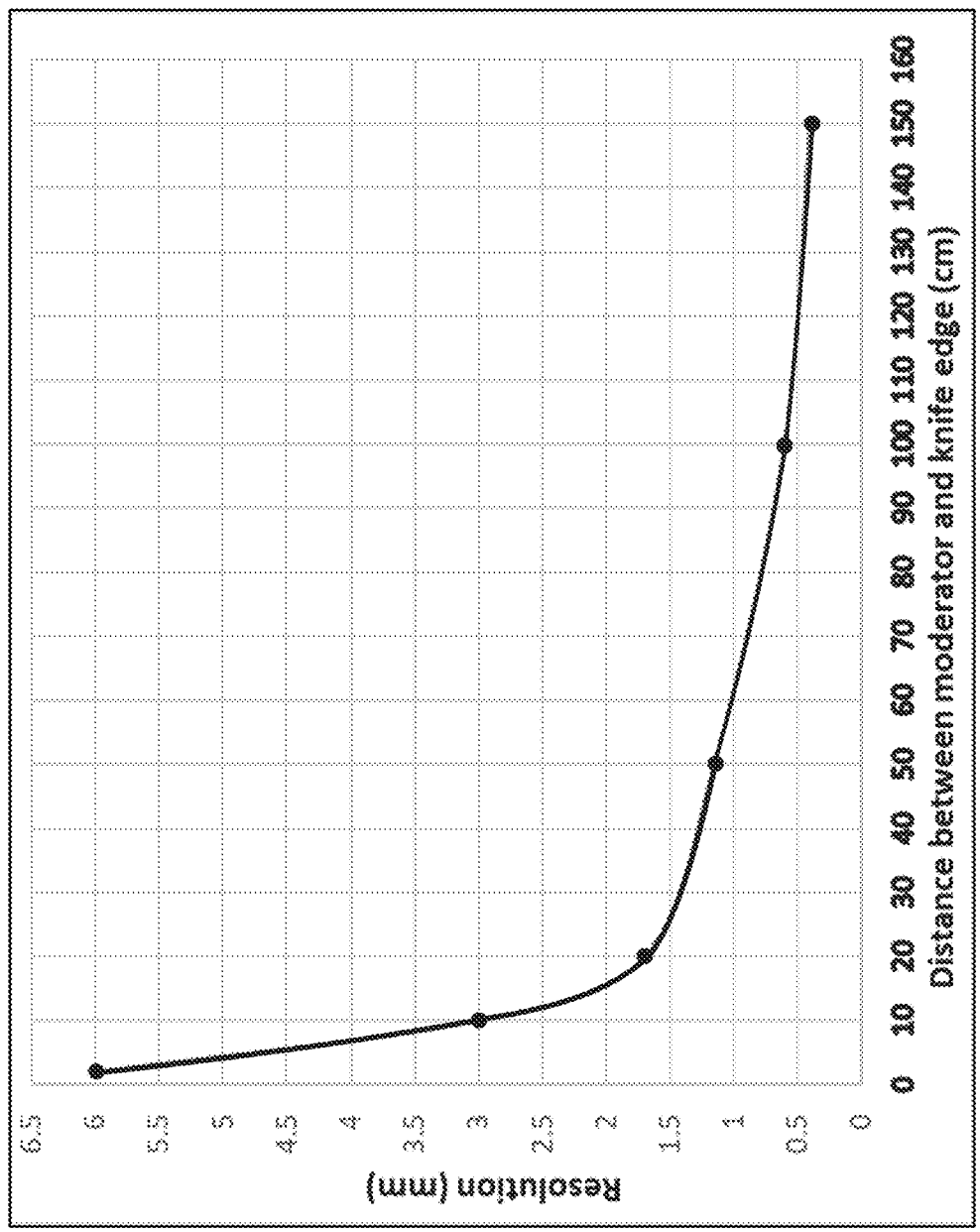
FIG. 8 is image resolution (mm) of the knife edge as a function of L, the distance between the end of BSA and the knife edge in an embodiment of the invention.

To improve the resolution, different parameters for $D_1$ and $D_2$ are selected, and different distances from the BSA aperture $D_2$ 228 to the knife edge are tried, L. All other parameters for the generator, knife edge and detector array are the same. Larger apertures $D_2$=5 cm, and $D_1$=8 cm. The distance to the knife edge L=2 cm. Flux as a function of x(cm) is shown in FIG. 7A. The maximum thermal flux is a healthy 3.4×10$^6$ n/cm$^2$-sec, but the resolution is 6-mm. Increasing the distance L to 100 cm, as shown in FIG. 7B, sub-mm resolution is achieved. Throughout these simulations, HDPE is used in both the moderator 108 and in the BSA 222, the thickness of the Moderator is $L_1$=4 cm, and the thickness of the BSA is $L_2$=4 cm. Plotting the resolution as a function of L in FIG. 8, the resolution continues to improve. We can achieve the desired resolutions of 1 mm for L=20 to 50 cm.

Figure 9:
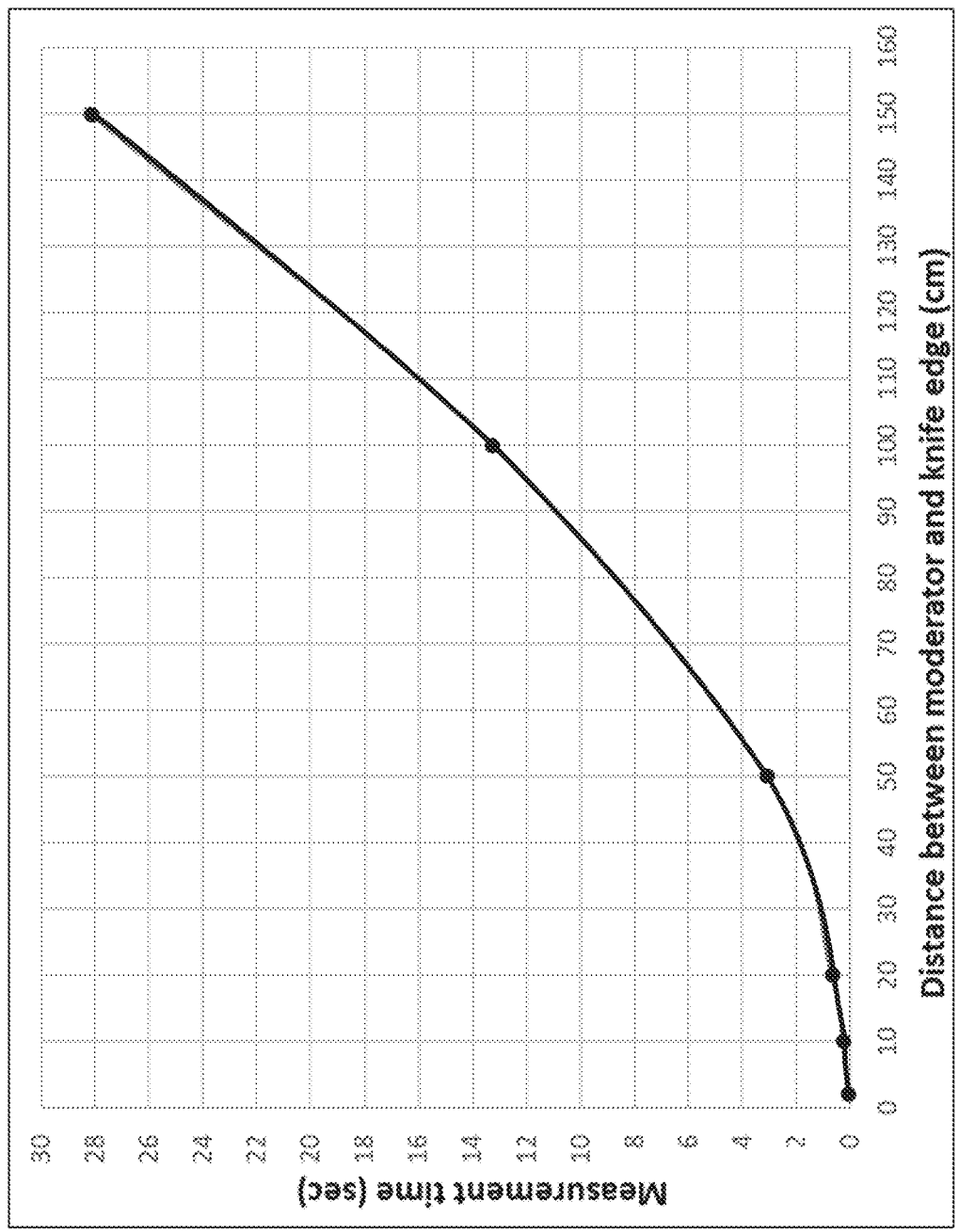
FIG. 9 shows estimated time (see) it takes to measure the knife edge as a function of L, the distance between the end of BSA and the knife edge in an embodiment of the invention.

However, with increasing distance L, the available neutron flux for imaging decreases resulting in an increase in measurement time for the collection of neutrons. This may be estimated with a simple assumption that each diode of the array needs around 250 neutrons for a measurement. Plotting the measurement time in FIG. 9 as a function of L, we see that we achieve measurement times in the order of seconds. With L=20 to 50 cm, the detection of the knife edge image with 1-mm resolution can take place within 1 to 3 seconds, a time more than adequate for achieving a high-quality image.

Convergent collimators are used throughout this submission, but divergent collimators or combinations of both convergent and divergent collimators may also be used. In the divergent conical collimator, the cone may be lined with grazing angle reflective materials such as Cadmium, Indium, $B_4C$ or Boron. The cone is made of a machinable material and lined with Cd, In, or B. The use of HDPE without a lining (Cd, In, or B) in the convergent collimator, as taught in this disclosure and demonstrated by MCNP simulation, ensures that both collection and further moderation of the neutrons to thermal energies can be achieved.

The resolution may further be improved by attenuating the fast neutrons by means of a low pass filter, in which thermal neutrons are transmitted, while fast neutrons are attenuated. Fast neutrons need to be attenuated or the detector's sensitivity to the fast neutrons needs to be suppressed. To eliminate fast neutrons, a 9-cm long sapphire crystal may be added to the BSA. Sapphire ($Al_2O_3$) is an effective fast-neutron filter because its transmission for neutrons of wavelengths less than 0.04 nm (500 meV) is less than 3% for a 100 mm thickness.

Current technology enables large diameter, single-crystal sapphire ingots to be grown using what is known as the Kyropoulos technique. Diameters of sapphire ingots may be 5 to 12 cm with thickness of 5 to 20 cm long. It is estimated that 7 cm of sapphire may reduce fast neutron yield by an order of magnitude while transmitting roughly 80% of the thermal neutron flux.

Figure 10A:
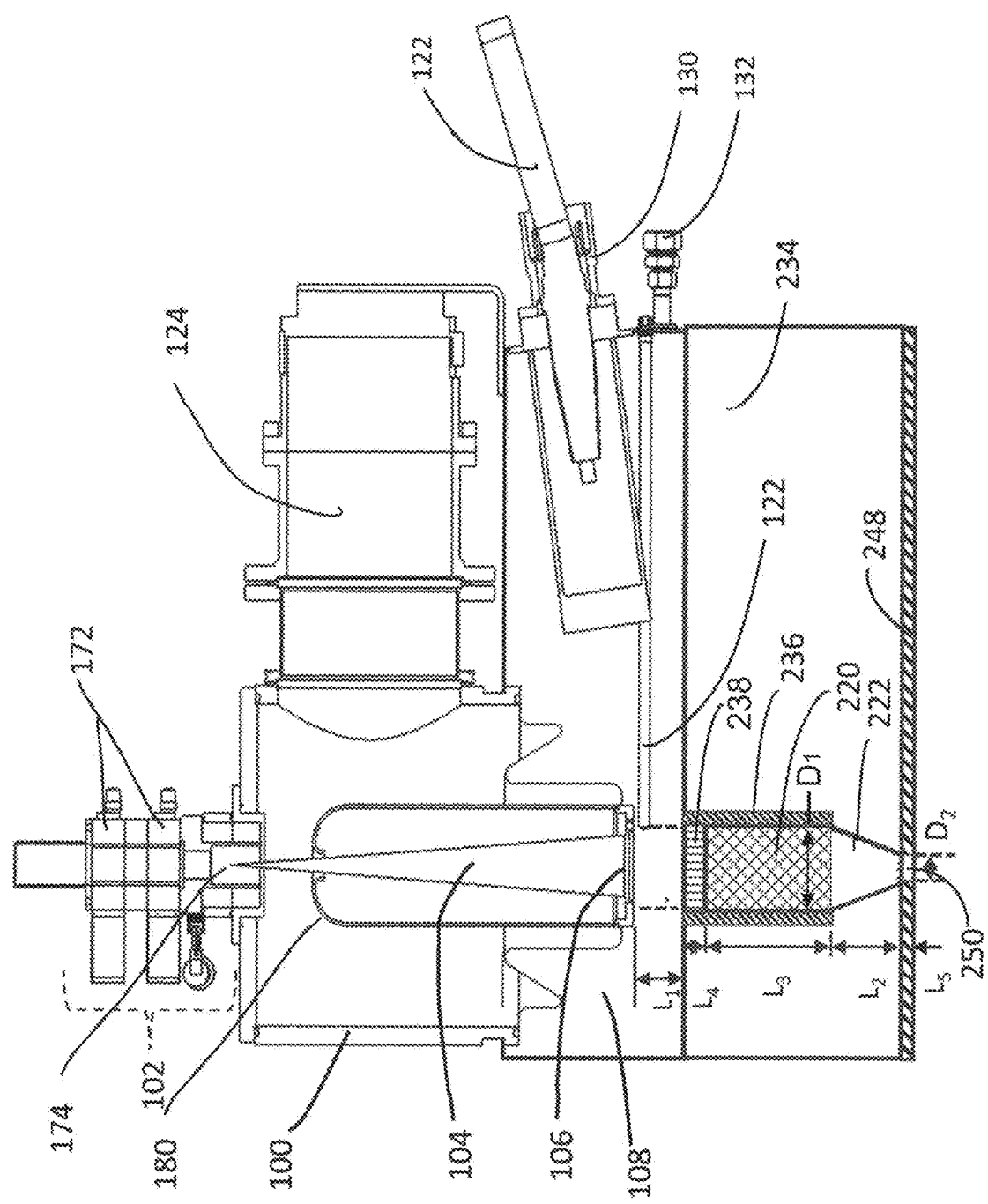
FIG. 10A is a longitudinal cross-sectional of the modular generator with a BSA composed of Bismuth foil, a funnel, an exit aperture, and a sapphire crystal with a reflecting graphite sleeve in an embodiment of the invention.
Figure 10B:
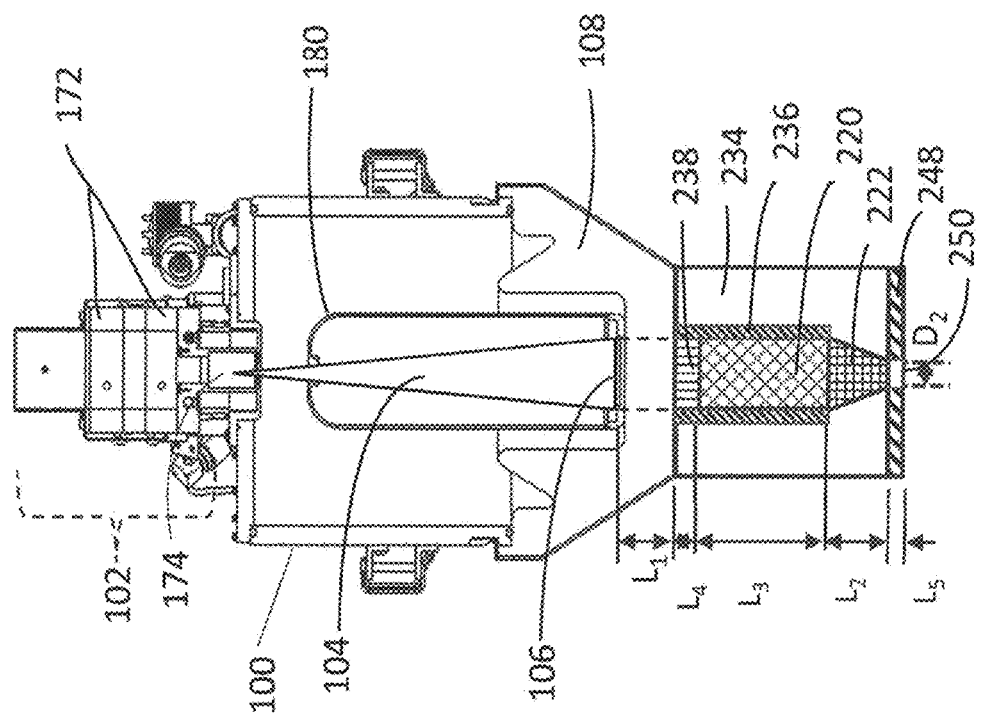
FIG. 10B is a transverse cross-section view of the modular generator of FIG. 10A taken along an axis of the acceleration chamber, and along the axis of a turbo vacuum pump in an embodiment of the invention.

FIGS. 10A and 10B show a modular generator with many of the same elements as shown in FIG. 3, but with additional detail of HDPE rectangular plate 234 and elements in a passage through plate 234 for filtering a neutron beam before the collimating funnel 222. Pre-moderator 108 using ~5.5 cm of HDPE produces in this example a neutron beam that is roughly equal in fast and thermal neutrons. As shown in FIGS. 10A and 10B a sapphire crystal 220 and a Bismuth filter 238 may be added that reduce the number of high energy gamma rays produced by thermal neutron capture of hydrogen in the HDPE. Sapphire crystal 220 in this embodiment may be a cylinder with an outer diameter fitting into sleeve 236, between 5 to 15 cm long with a high enough average atomic number, Z, to attenuate the gamma background. Bismuth filter 238 is a disk of the diameter of the sapphire crystal fitting into sleeve 236 just above the sapphire crystal. Sapphire filter 220 is added just below the pre-moderator 108 and into a sleeve 236 which encloses the sapphire filter 220, acts as a reflector and attenuates the neutrons that are outside the sapphire crystal 220. A funnel 222 which is $L_2$=4 cm long and a reducing aperture $D_1$ which directs the thermal neutrons to the desired minimal aperture $D_2$ for a desired small beam diameter $D_2$. It is important to minimize the distance ($L_1+L_2+L_3+L_4+L_5$) from the Ti target 106, to the aperture $D_2$, 250. This maximizes the thermal neutron yield delivered to the small aperture $D_2$, while minimizing spurious radiation of gammas and fast neutrons. This maximizes the number of thermal neutrons required for good image resolution and contrast.

The $D^+$ ion beam 104 strikes the titanium target 106, where $D^+$ ions are embedded and creates the DD fusion reaction, resulting in the isotropic emission of fast (2.5 MeV) neutrons. To maximize the flux being transmitted through the sapphire filter, the crystal 220 is aligned with its axis in line with the ion beam 104 direction and the maximum incoming thermal neutron beam. The sapphire crystal length and orientation is selected to maximize the thermal neutron transmission preferably in a wavelength range of 1.2 to 2.5 A, while minimizing fast neutron wavelengths of less than 1 Angstrom. Fast neutron transmission, T, decreases exponentially with crystal length, L: or $T=I/I_o=\exp(-L/L_o)$. In this embodiment a sapphire crystal length of 70 mm is selected, which roughly gives an order of magnitude decrease in the fast neutrons relative to the thermal.

Assuming a mixed neutron beam is being transmitted thru the Sapphire filter, it is desired to maximize the thermal neutrons while suppressing the fast and epithermal neutron components and the gamma rays produced in the HDPE pre-moderator material. It is desired in this example to maximize transmission of a 2.5 cm beam, defined by the definition of Full Width Half Maximum (FWHM), of thermal neutrons down a cylinder 220 composed of Sapphire crystal. Thermal neutrons are being scattered during transmission and some are lost outside the sapphire crystal. However, a sleeve 236 of high density (or high Z) reflecting material just outside the crystal surface may reflect the thermal neutrons back into the crystal and thereby increase the total neutron yield at the exit to the BSA. In this example the sleeve 236 is Bismuth surrounding the sapphire crystal. The high Z sleeve critical angle reflects any grazing-angle thermal neutrons but scatters and absorbs the higher energy neutrons that pass from the sapphire to the Bismuth. Ideally, the thermal neutrons travel down the sapphire cylinder and the fast neutrons get absorbed or scattered. The conical aperture at the end of the Sapphire crystal acts to transmit the thermal flux out a small aperture ($D_2$). The conical aperture 228 diameter tapers from $D_1$=6 cm to $D_2$=1.5 cm. in this implementation There are other parameters and materials, such as graphite, that can be used to form the conical aperture 222 and the rectangular plate 234.

Because tungsten target 106 is on the plastic (HDPE or Teflon) pre-moderator 108, fast neutrons coming from the target immediately enter the pre-moderator and can be moderated to thermal or epithermal energies. A short Beam Shaping Assembly (BSA) is provided below the Ti target and the pre-moderator, where some of the thermal neutrons may be collected and directed to a small aperture at the end of the BSA. A short, $L_5$, iris 250 is placed just below the BSA. The material of the iris 250 may be made of lead and $B_4C$. In its simplest embodiment, the BSA is an inverted cone 222 as shown in FIGS. 3A and 3B. The HDPE of the BSA acts as a reflector and collimator of the thermal neutrons. As stated elsewhere, the collimator can be made of other materials such as graphite. The resulting thermal neutron beam at the aperture of the BSA gives a higher flux and smaller source size for the thermal neutrons when compared to a simple moderator. In the example shown, the spot size is roughly 1.5 cm in Diameter ($D_2$). Without the BSA the diameter of the source size at the pre-moderator would be a disc 6 cm in diameter and expanding. The idea behind the use of the pre-moderator 108 in direct or near contact with Titanium target 106 is to produce a maximum thermal neutron flux. Adding a BSA of modest thickness ($L_2$=4 cm in this example) directly on to the pre-moderator permits a maximum number of neutrons and higher thermal neutron flux to be collected and a smaller source size to be obtained. The close stacking of the pre-moderator and the BSA permits a maximum number of thermal neutrons to be obtained with a small source size $D_2$.

In embodiments of the invention, thermal neutron collection can be achieved with a conical funnel to both collect and channel neutrons into a small spot size with increased thermal flux at the exit of the cone of the funnel. The compact DD fusion source with a short thermal moderator (such as HDPE, or UHMW plastics with a high concentration of hydrogen atoms) quickly scatters the fast 2.5 MeV neutrons to thermal energies in a short distance ($L_1+L_2+L_3+L_4+L_5$) from the fast neutron source (the titanium target 106). As shown in FIGS. 3A and 3B, the neutrons are then collected by a relatively short (e.g., $L_2$=3 to 4 cm) funnel 222 in the slab of HDPE. Both moderation and scattering continue to occur along the cone length L. Simulations show that this results in an increase in flux 2 to 3 times and spot sizes of 1 to 3 cm in diameter depending on the geometry of the cone and size of the fast neutron emitter (Ti target). Additions of short spatial and energy filters improve the image by improving the brightness of the neutron source and limiting the effects of spurious radiation of fast neutrons, gamma emission.

In embodiments of the invention, the shortness and compactness of the DD fusion generator and the moderation process to produce and collect thermal neutrons also allows for the use of other devices in the beam including short lengths of sapphire 220 and bismuth crystals 240, which can reduce the fast neutrons and gamma emission in the neutron beam, thus cleaning up the beam and achieving a beam of thermal neutrons at the cancer site. The use of a compact fusion generator with relatively small spot sources of neutrons permits these neutron filters to also be compact and close together. This results in a useful source of neutrons that can be used in many laboratories and field locations, unlike the fixed, large and expensive reactor sources.

In another aspect of the invention a unique beam-shaping apparatus (BSA) is provided for use with a low-voltage fusion generator (LVFG) for focused treatment of tumors in an application of Boron Neutron Capture Therapy. BNCT, as described above, is a selective radiation treatment for tumors that are caused accumulate drugs carrying the stable boron isotope, 10B. BNCT has been evaluated clinically as an alternative to conventional radiation therapy for the treatment of tumors. Both a drug carrying 10B and thermal neutrons rust be delivered to the cancer site.

Figure 11:
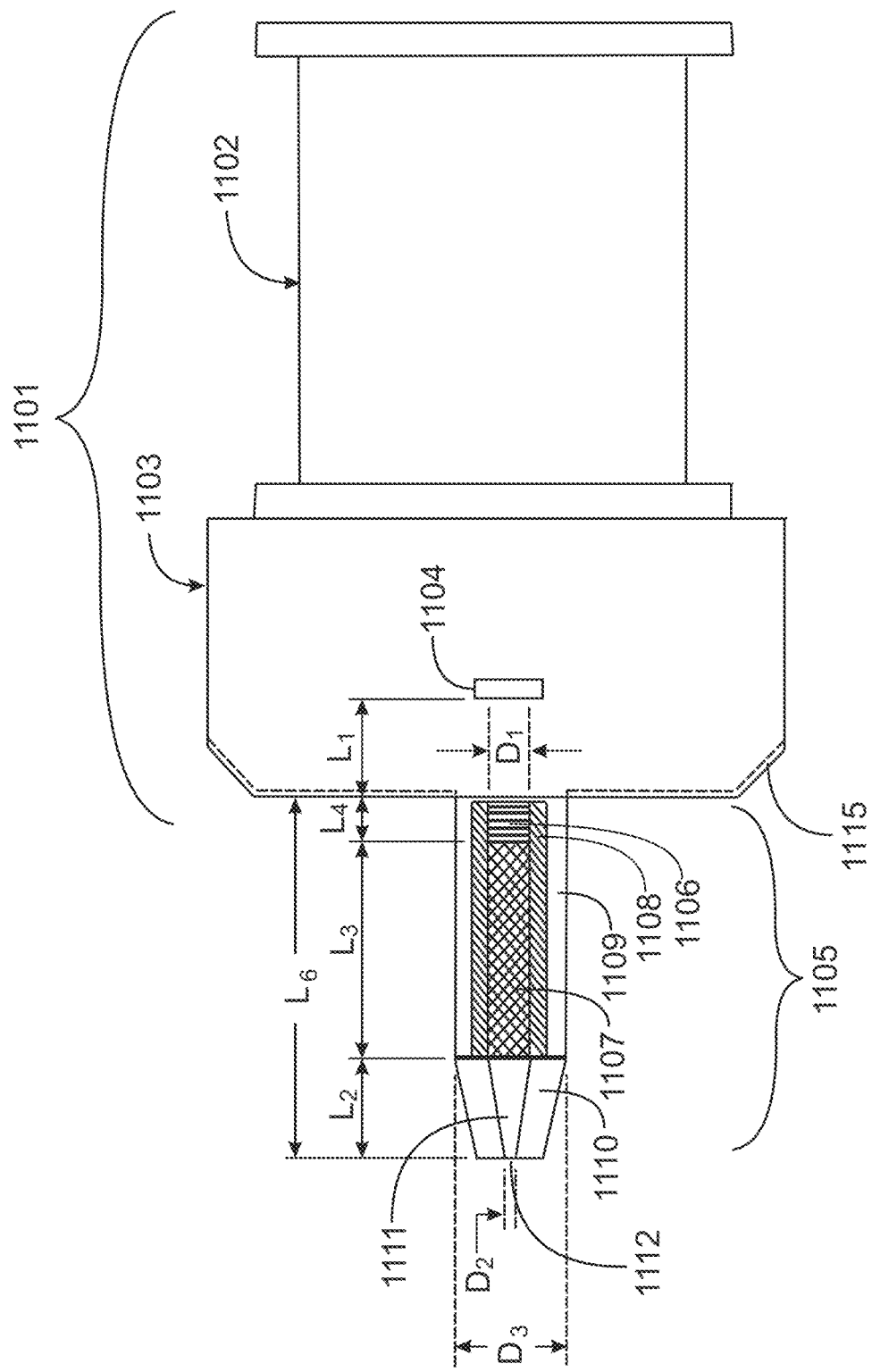
FIG. 11 is an elevation view of a low-voltage fusion generator (LVFG) with a beam-shaping apparatus (BSA) in an embodiment of the invention.
Figure 12:
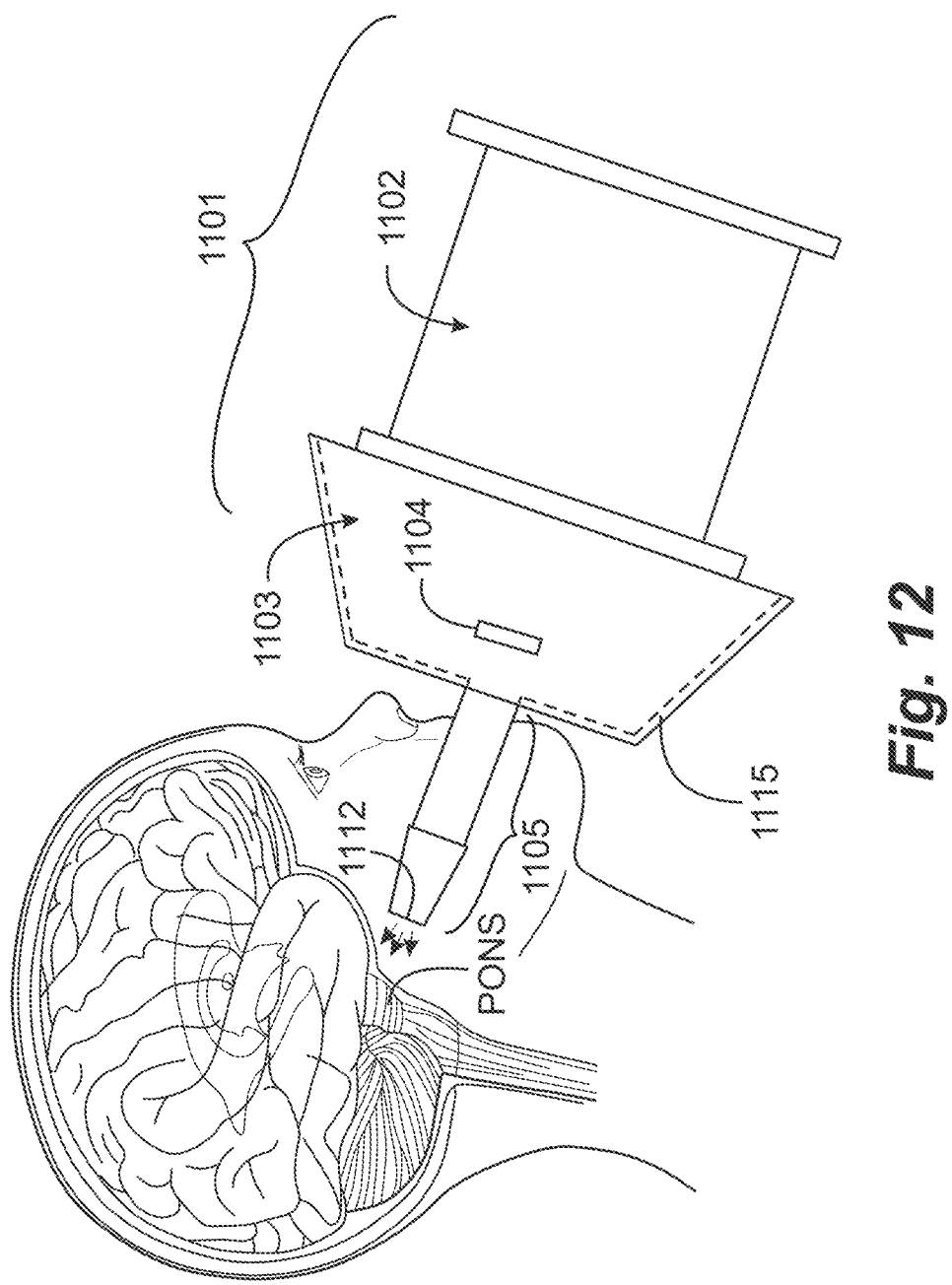
FIG. 12 is a diagram showing the LVFG with BSA applied to treat a tumor in a base of a brain of a subject.
Figure 13:
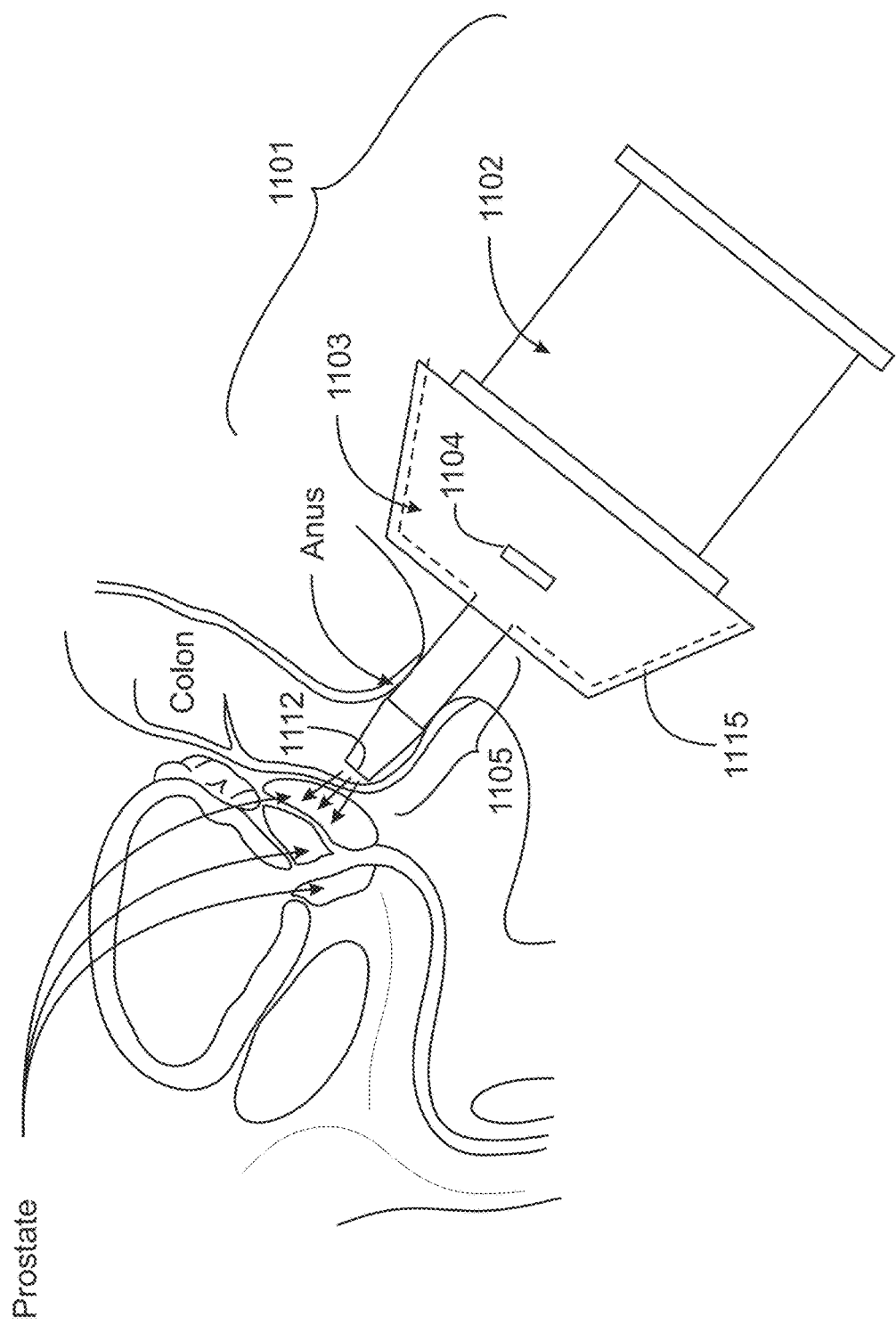
FIG. 13 is a diagram showing the LVFG with BSA applied to treat a tumor in a prostate gland of a subject.

FIG. 11 is an elevation view of a low-voltage fusion generator (LVFG) 1101 with a unique beam-shaping apparatus (BSA) 1105 in an embodiment of the invention. FIG. 12 is a diagram showing LVFG 1101 with BSA 1105 applied to treat a tumor Diffuse Intrinsic Pontine Glioma (DIPG). FIG. 13 is a diagram showing LVFG 1101 with BSA 1105 applied to treat a tumor in a prostate gland of a subject.

LVFG 1101 in FIG. 11 in one embodiment may be identical or very similar to LVFG 118 described in detail above, but in other embodiments may be different, with a common requirement that the generator produce a flux of thermal neutrons at an entrance to a BSA 1105.

Compact BSA 1105 is, in this example, an elongated tubular structure having an overall length $L_{10}$ from a base surface of moderator 1103, and a maximum diameter $D_5$. This structure has been termed by the inventor a Compact Oncologic Neutron Source (CONS). $L_{10}$ may be in different embodiments from about 3 inches in length to about 10 inches. The length in different embodiments may depend at least in part on an intended use of the apparatus. For example, for the purpose depicted in FIG. 12, that of extending into a subject's oral cavity to emit neutrons proximate the PONS at the back of the subject's throat, $L_{10}$ may be about 6 inches. The maximum diameter $D_5$ for the purpose depicted by FIG. 12 may be, for example about 1 inch, but may vary somewhat for models for application to different subjects.

For the purpose of treating a tumor in a subject's prostate gland, as shown in FIG. 13 $L_{10}$ may be somewhat less than six inches, and overall diameter $D_5$ may be greater, such as up to 2 inches in diameter. In either case BSA 1105 is a relatively long and relatively narrow tubular structure.

The geometry and size of BSA 1105 enables positioning and focusing of neutrons at specific points on a human body with minimization of more harmful emission components that may damage healthy tissue. LVFG 1101 produces, in this example, a mixture of fast and thermal neutrons after passing through pre-moderator 1103 of about 5.5 cm of HDPE. The fast neutrons are moderated by pre-moderator 1103 to approximately 50% thermal energies and 50% fast neutrons in this example. Hard x-rays are also typically produced. The fast neutrons and the hard x-rays do not contribute to helpful $n_{th}$+1B reaction and are harmful to healthy tissue, so need to be eliminated from the neutron beam and the remaining thermal neutrons $n_{th}$ collected. Only the thermal neutrons are effective in the Boron neutron interaction and destruction of the cancer cells. Filtering of the harmful components and the collection of the thermal neutrons by the BSA 314 designed for use in radiography, shown in FIGS. 10A and 10B, does just that.

BSA 1105 and pre-moderator 1103 may be adjusted for optimum neutron energy at the cancer site by material selection and optimum dimensions. Pre-moderator slab 1103 may be reduced in size and shaped to permit close contact with a human body. In FIG. 11 the BSA along with the LVFG is shown being used to irradiate tumors at the PONS and in FIG. 13 the BSA is positioned in the anus to irradiate cancer at the prostate. In both cases the BSA is placed at these locations without surgery. In FIG. 11 the BSA is positioned in the mouth and directed to the PONS which is anterior to the plate at the roof of the mouth. This brings neutron emission as close as possible to the PONS without surgery with the neutrons directed to the top of the spinal column where the PONS is located.

As shown in FIG. 11 in this example a sapphire crystal 1107 and a Bismuth filter 1106 are positioned to reduce high energy gamma rays produced by thermal neutron capture of hydrogen in the HDPE. Sapphire crystal 1107 in this embodiment is a cylinder with an outer diameter fitting into an inner sleeve 1108, the sleeve of a material with a high enough average atomic number, Z, to attenuate the gamma background. Bismuth filter 1106 is a disk of the diameter of the sapphire crystal fitting into sleeve 1108 just above the sapphire crystal. A funnel 1111 which is in this example about $L_7$=4 cm long provides a reducing aperture which directs the thermal neutrons to a desired minimal aperture $D_4$ for a desired small beam diameter. It is important to minimize the distance ($L_6+L_7+L_8+L_9$) from the Ti target 1104: to the aperture $D_4$, 1112. This maximizes the thermal neutron yield delivered to the small aperture $D_4$, while minimizing spurious radiation of gammas and fast neutrons. This maximizes the number of thermal neutrons required for maximum dose to the cancer site.

Neutron and gamma ray shielding 1115 is shown in FIGS. 12 and 13 positioned into and along the surface of the pre-moderator slab 1103 to minimize radiation to the patient outside the cancer zone. This shielding protects the subject from harmful radiation otherwise escaping from pre-moderator slab 1103. The shielding 1115 may be made of several layers of Gd, W or $B_4C$, or as combination of one or more of these materials. Gd is good at stopping thermal neutrons, W stops gamma rays and B4C both.

The main objective of shielding 1115 is to reduce harmful radiation to health tissue, but the trade-off is the that the thermal radiation going to the cancer site is also reduced because of the increase in the distance from the patient to the neutron source $L_{10}+L_6$. To minimize the harmful radiation the time between doses is limited by turning the generator on and off but still administering a "kill" dose to the cancer cells. The make sure the dose is adequate, the shielding 1115 is made thin.

In addition to disk 1106 and cylindrical crystal 1107, both encased in inner sleeve 1108, BSA 1105 further comprises an outer sleeve 1109 and an outer covering 1110 on funnel 1111 which may be in this example high-density Polyethylene (HDPE) or Ultra High Molecular Weight (UHMW) polyethylene. These materials are selected to minimize the patent's contact with toxic materials (such a Bi and Pb) and further reduce neutrons and gammas not directed by the conical optic to the cancer site.

By bringing the BSA to the locations illustrated radiation can be positioned on a cancer site while a minimum of healthy tissue is irradiated. In addition, the LVFG is much smaller than a reactor or linear accelerator and, with a suitable BSA as described, can be easily positioned compared to these devices for directing and positioning the neutron beam to the cancer site. The LVFG and its accompanied BSA can be rotated and moved using a small gantry unlike a linear accelerator or reactor, which are much larger and, in most cases, cannot be moved at all and the patient must be aligned and positioned to the apparatus.

A lack of treatment options and a fact that almost all DIPG patients die within two years of diagnosis make DIPG research an important and immediate need. Unfortunately, treatment options for DIPG are limited. The tumors cannot be removed surgically because the tumor cells are all intermixed with the normal cells in the brainstem that are crucial for functions like breathing. Gamma Radiation to the tumor is the only therapy that has been proven to shrink these tumors and let children with DIPG live longer, but even radiation cannot make the tumor go away permanently because the amount of radiation is damaging both to cancer cells and healthy cells. The use of BNCT targets the cancer cells which have preferentially absorbed boron. Targeting the cancer site with the CONS further reduces the radiation to health tissue while BNCT further increases cancer cell death.

The skilled person will understand that the examples depicted and described in this application are entirely exemplary and are not limiting to the scope of the invention. Dimensions may vary in different applications, and materials and construction details may vary as well. The scope of the invention is limited only by the claims.

The invention claimed is:

1. A cancer treatment apparatus, comprising:
a neutron source generating neutrons exiting through a surface of a moderator block; and
an elongated beam-shaping apparatus (BSA) having a length and a circular cross section of a diameter less than the length, the BSA joined at one end to and projecting orthogonally from the surface of the moderator block of the neutron source, the BSA having a conically shaped element at an end away from the moderator block, the conically shaped element declining in diameter in a direction away from the moderator block;
wherein neutrons produced by the neutron source enter the BSA at the surface of the moderator block, travel the length of the BSA, and exit the BSA through an aperture at the end of the BSA away from the moderator block.

2. The cancer treatment apparatus of claim 1 wherein the BSA further comprises an outer sleeve encasing a concentric inner sleeve encasing a bismuth disk in line with a sapphire crystal cylinder, and a funnel cavity within the conically-shaped element at the end away from the moderator block;
wherein neutrons exiting the moderator block through the surface proximate the BSA pass through the bismuth disk and the sapphire crystal, enter the funnel and are collimated through the funnel to exit through the aperture at the end of the BSA, providing a neutron beam with a spot size useful for neutron irradiation of a tumor.

3. The cancer treatment apparatus of claim 1 wherein the moderator block is made of one or a combination of high-density polyethylene (HDPE), Teflon, Ultra High Molecular Weight polyethylene, or graphite.

4. The cancer treatment apparatus of claim 2 wherein the outer sleeve is high-density polyethylene (HDPE) or Ultra High Molecular Weight polyethylene.

5. The cancer treatment apparatus of claim 1 wherein the length of the BSA is between three inches and ten inches, inclusive.

6. The cancer treatment apparatus of claim 1 wherein the outside diameter of the BSA is between three-quarters of an inch and two inches inclusive.

7. The cancer treatment apparatus of claim 2 wherein the length of the funnel is from 1 to 10 inches, inclusive.

8. The cancer treatment apparatus of claim 1 wherein the aperture at the end of the BSA away from the moderator block has a diameter of from 0.38 inches to 0.75 inches inclusive.

9. A method for treating a subject for a tumor at the PONS, comprising:
joining an elongated beam-shaping apparatus (BSA) having a length and a circular cross section of a diameter less than the length to project orthogonally from a first end from a surface of a moderator block of a neutron source generating neutrons exiting through the surface of a moderator block into the BSA, the BSA having a conically shaped funnel at an end away from the moderator block, the conically-shaped element declining in diameter in a direction away from the moderator block and ending at an emission aperture at a second end away from the moderator block;
placing the subject on a support proximate to the neutron source;
positioning the BSA in an oral cavity of the subject with the emission aperture proximate the tumor site at the PONS; and
irradiating the tumor for a period of time with neutrons emitted from the emission aperture.

10. The method of claim 9 further comprising a step for ensuring the neutron source is powered off, not generating neutrons, during the time the subject and the apparatus are manipulated to position the BSA in the oral cavity, and a step for powering on the neutron source to treat the tumor after the subject and the apparatus positioned for treatment.

11. The method of claim 9 wherein the BSA further comprises an outer sleeve encasing a concentric inner sleeve encasing a bismuth disk in line with a sapphire crystal cylinder, and a funnel cavity within the conically-shaped element at the end away from the moderator block, and wherein neutrons exiting the moderator block through the surface proximate the BSA pass through the bismuth disk and the sapphire crystal, enter the funnel and are collimated through the funnel to exit through the aperture at the end of the BSA.

12. The method of claim 9 wherein the moderator block is made of one or a combination of high-density polyethylene (HDPE), Teflon, Ultra High Molecular Weight polyethylene, or graphite.

13. The method of claim 11 wherein the outer sleeve is high-density polyethylene (HDPE) or Ultra High Molecular Weight polyethylene.

14. A method for treating a subject for-tumors at the prostate gland, comprising:
joining an elongated beam-shaping apparatus (BSA) having a length and a circular cross section of a diameter less than the length to project orthogonally from a first end from a surface of a moderator block of a neutron source generating neutrons exiting through the surface of a moderator block into the BSA, the BSA having a conically shaped funnel at an end away from the moderator block, the conically-shaped element declining in diameter in a direction away from the moderator block and ending at an emission aperture at a second end away from the moderator block;
placing the subject on a support proximate to the neutron source;
positioning the BSA in an anal cavity of the subject with the emission aperture proximate the tumor site at the prostate gland; and
irradiating the tumor for a period of time with neutrons emitted from the emission aperture.

15. The method of claim 14 further comprising a step for ensuring the neutron source is powered off, not generating 4 neutrons, during the time the subject and the apparatus are manipulated to position the BSA in the oral cavity, and a step for powering on the neutron source to treat the tumor after the subject and the apparatus positioned for treatment.

16. The method of claim 14 wherein the BSA further comprises an outer sleeve encasing a concentric inner sleeve encasing a bismuth disk in line with a sapphire crystal cylinder, and a funnel cavity within the conically-shaped element at the end away from the moderator block, and wherein neutrons exiting the moderator block through the surface proximate the BSA pass through the bismuth disk and the sapphire crystal, enter the funnel and are collimated through the funnel to exit through the aperture at the end of the BSA.

17. The method of claim 14 wherein the moderator block is made of one or a combination of high-density polyethylene (HDPE), Teflon, Ultra High Molecular Weight polyethylene, or graphite.

18. The method of claim 15 wherein the outer sleeve is high-density polyethylene (HDPE) or Ultra High Molecular Weight polyethylene.

* * * * *